United States Patent
Jung et al.

(10) Patent No.: US 10,017,546 B2
(45) Date of Patent: Jul. 10, 2018

(54) MONOMERIC AVIDIN-LIKE PROTEINS WITH STABLE BIOTIN BINDING ABILITY

(71) Applicant: KOREA ADVANCED INSTITUTE OF SCIENCE AND TECHNOLOGY, Daejeon (KR)

(72) Inventors: Yong Won Jung, Daejeon (KR); Jeong Min Lee, Daejeon (KR)

(73) Assignee: KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 191 days.

(21) Appl. No.: 15/196,533

(22) Filed: Jun. 29, 2016

(65) Prior Publication Data

US 2017/0114104 A1 Apr. 27, 2017

(30) Foreign Application Priority Data

Oct. 26, 2015 (KR) .................. 10-2015-0148989

(51) Int. Cl.
  *C07K 14/195* (2006.01)
  *C07K 14/77* (2006.01)
  *C07K 14/47* (2006.01)

(52) U.S. Cl.
  CPC .......... *C07K 14/195* (2013.01); *C07K 14/47* (2013.01); *C07K 2319/00* (2013.01); *C07K 2319/24* (2013.01)

(58) Field of Classification Search
  None
  See application file for complete search history.

(56) References Cited

U.S. PATENT DOCUMENTS 4,554,101 A 11/1985 Hopp .................. 260/112.5

OTHER PUBLICATIONS

DeMonte, D., et al., (2013). "Structure-based engineering of streptavidin monomer with a reduced biotin dissociation rate". *Proteins* 81:1621-1633.
Dundas, C., et al., (2013). "Streptavidin-biotin technology: improvements and innovations in chemical and biological applications". *Appl Microbiol Biotechnol* 97:9343-9353.
Howarth, M., et al., (2006). "A monovalent streptavidin with a single femtomolar biotin binding site". *Nature Methods* 3(4):267-273.
Howarth, M., et al., (2008). "Monovalent, reduced-size quantum dots for imaging receptors on living cells". *Nature Methods* 5(5):397-399.
Laitinen, O., et al., (2003). "Rational design of an active avidin monomer". *The Journal of Biological Chemistry* 278(6):4010-4014.
Laitinen, O., et al (2007). "Brave new (strept)avidins in biotechnology". *TRENDS in Biotechnology* 25(6):269-277.
Lim, K.H., et al., (2012). "Stable, high-affinity streptavidin monomer for protein labeling and monovalent biotin detection". *Biotechnology and Bioengineering* 110(1):57-67.
Qureshi, M., et al., (2002). "Design, production, and characterization of a monomeric streptavidin and its application for affinity purification of biotinylated proteins". Protein Expression and Purification 25:409-415.

*Primary Examiner* — Marsha M Tsay
(74) *Attorney, Agent, or Firm* — Harness, Dickey & Pierce, P.L.C.

(57) ABSTRACT

Disclosed are monomeric avidin-like proteins with a strong and stable biotin-binding ability, protein conjugates containing two or more of the monomeric avidin-like proteins and having a multivalent binding ability to biotin, nucleic acid molecules for encoding the monomeric avidin-like proteins, and methods for producing the monomeric avidin-like proteins, so the monomeric avidin-like proteins, due to the monomeric structure, are free from a problem of the disruption of receptor functions, caused by oligomerization occurring in existing tetrameric streptavidin or tetrameric but monovalent streptavidin variants.

12 Claims, 21 Drawing Sheets

SEQUENCE LISTING

```
<160> NUMBER OF SEQ ID NOS: 10

<210> SEQ ID NO 1
<211> LENGTH: 128
<212> TYPE: PRT
<213> ORGANISM: Artificial Sequence
<220> FEATURE:
<223> OTHER INFORMATION: amino acid sequence of truncated Rhizavidin

<400> SEQUENCE: 1

Phe Asp Ala Ser Asn Phe Lys Asp Phe Ser Ser Ile Ala Ser Ala Ser
1               5                   10                  15

Ser Ser Trp Gln Asn Gln Ser Gly Ser Thr Met Ile Ile Gln Val Asp
            20                  25                  30

Ser Phe Gly Asn Val Ser Gly Gln Tyr Val Asn Arg Ala Gln Gly Thr
        35                  40                  45

Gly Cys Gln Asn Ser Pro Tyr Pro Leu Thr Gly Arg Val Asn Gly Thr
    50                  55                  60

Phe Ile Ala Phe Ser Val Gly Trp Asn Asn Ser Thr Glu Asn Cys Asn
65                  70                  75                  80

Ser Ala Thr Gly Trp Thr Gly Tyr Ala Gln Val Asn Gly Asn Asn Thr
                85                  90                  95

Glu Ile Val Thr Ser Trp Asn Leu Ala Tyr Glu Gly Gly Ser Gly Pro
            100                 105                 110

Ala Ile Glu Gln Gly Gln Asp Thr Phe Gln Tyr Val Pro Thr Thr Glu
        115                 120                 125

<210> SEQ ID NO 2
<211> LENGTH: 128
<212> TYPE: PRT
<213> ORGANISM: Artificial Sequence
<220> FEATURE:
<223> OTHER INFORMATION: amino acid sequence of mRA

<400> SEQUENCE: 2

Phe Asp Ala Ser Asn Phe Lys Asp Phe Ser Ser Ile Ala Ser Ala Ser
```

```
                1               5                    10                   15
Ser Ser Trp Gln Asn Gln Ser Gly Ser Thr Met Ile Ile Gln Val Asp
                20                   25                   30

Ser Phe Gly Asn Val Ser Gly Gln Tyr Val Asn Arg Ala Gln Gly Thr
                35                   40                   45

Gly Cys Gln Asn Ser Pro Tyr Pro Leu Thr Gly Arg Val Asn Gly Thr
        50                   55                   60

Phe Ile Asp Phe Ser Val Lys Trp Asn Asn Ser Thr Glu Asn Cys Asn
65                   70                   75                   80

Ser Asn Thr Gln Trp Thr Gly Tyr Ala Gln Val Asn Gly Asn Thr
                85                   90                   95

Glu Ile Val Thr Arg Trp Asn Leu Lys Tyr Glu Gly Gly Ser Gly Pro
                100                  105                  110

Ala Ile Glu Gln Gly Gln Asp Thr Phe Gln Tyr Val Pro Thr Thr Glu
                115                  120                  125

<210> SEQ ID NO 3
<211> LENGTH: 128
<212> TYPE: PRT
<213> ORGANISM: Artificial Sequence
<220> FEATURE:
<223> OTHER INFORMATION: amino acid sequence of MA

<400> SEQUENCE: 3

Phe Asp Ala Ser Asn Phe Lys Asp Phe Ser Ser Ile Ala Ser Ala Ser
1               5                    10                   15

Ser Ser Trp Gln Asn Gln His Gly Ser Thr Met Ile Ile Gln Val Asp
                20                   25                   30

Ser Phe Gly Asn Val Ser Gly Gln Tyr Val Asn Arg Ala Glu Gly Thr
                35                   40                   45

Gly Cys Gln Asn Ser Pro Tyr Pro Leu Thr Gly Arg Val Asn Gly Thr
        50                   55                   60

Phe Ile Asp Phe Ser Val Lys Trp Asn Asn Ser Thr Glu Asn Cys Asn
65                   70                   75                   80

Ser Asn Thr Gln Trp Thr Gly Tyr Ala Gln Val Asn Gly Asn Thr
                85                   90                   95

Glu Ile Val Thr Arg Trp Asn Leu Lys Tyr Glu Gly Gly Ser Gly Pro
                100                  105                  110

Ala Ile Trp Gln Gly Gln Asp Thr Phe Gln Tyr Val Pro Thr Thr Glu
                115                  120                  125

<210> SEQ ID NO 4
<211> LENGTH: 15
<212> TYPE: PRT
<213> ORGANISM: Artificial Sequence
<220> FEATURE:
<223> OTHER INFORMATION: amino acid sequence of biotin-AP

<400> SEQUENCE: 4

Gly Leu Asn Asp Ile Phe Glu Ala Gln Lys Ile Glu Trp His Glu
1               5                    10                   15

<210> SEQ ID NO 5
<211> LENGTH: 249
<212> TYPE: PRT
<213> ORGANISM: Artificial Sequence
<220> FEATURE:
<223> OTHER INFORMATION: amino acid sequence of biotin-GFP

<400> SEQUENCE: 5
```

```
Met Gly Leu Asn Asp Ile Phe Glu Ala Gln Lys Ile Glu Trp His Glu
1               5                   10                  15

Gly Gly Gly Gly Ser Lys Gly Glu Glu Leu Phe Thr Gly Val Val Pro
                20                  25                  30

Ile Leu Val Glu Leu Asp Gly Asp Val Asn Gly His Glu Phe Ser Val
                35                  40                  45

Arg Gly Glu Gly Glu Gly Asp Ala Thr Ile Gly Lys Leu Thr Leu Lys
50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Arg His Asp Phe Phe Lys Ser Ala Met Pro Glu Gly Tyr Val
                100                 105                 110

Gln Glu Arg Thr Ile Ser Phe Lys Asp Asp Gly Lys Tyr Lys Thr Arg
                115                 120                 125

Ala Val Val Lys Phe Glu Gly Asp Thr Leu Val Asn Arg Ile Glu Leu
            130                 135                 140

Lys Gly Thr Asp Phe Lys Glu Asp Gly Asn Ile Leu Gly His Lys Leu
145                 150                 155                 160

Glu Tyr Asn Phe Asn Ser His Asp Val Tyr Ile Thr Ala Asp Lys Gln
                165                 170                 175

Glu Asn Gly Ile Lys Ala Glu Phe Thr Val Arg His Asn Val Glu Asp
                180                 185                 190

Gly Ser Val Gln Leu Ala Asp His Tyr Gln Gln Asn Thr Pro Ile Gly
                195                 200                 205

Asp Gly Pro Val Leu Leu Pro Asp Asn His Tyr Leu Ser Thr Gln Thr
            210                 215                 220

Val Leu Ser Lys Asp Pro Asn Glu Lys Arg Asp His Met Val Leu His
225                 230                 235                 240

Glu Tyr Val Asn Ala Ala Gly Ile Thr
                245

<210> SEQ ID NO 6
<211> LENGTH: 76
<212> TYPE: PRT
<213> ORGANISM: Artificial Sequence
<220> FEATURE:
<223> OTHER INFORMATION: amino acid sequence of biotin-protein G

<400> SEQUENCE: 6

Met Gly Leu Asn Asp Ile Phe Glu Ala Gln Lys Ile Glu Trp His Glu
1               5                   10                  15

Gly Gly Gly Gly Ser Thr Tyr Lys Leu Val Ile Asn Gly Lys Thr Leu
                20                  25                  30

Lys Gly Glu Thr Thr Thr Lys Ala Val Asp Ala Glu Thr Ala Glu Lys
            35                  40                  45

Cys Phe Lys Gln Tyr Ala Asn Asp Asn Gly Val Asp Gly Val Trp Thr
50                  55                  60

Tyr Asp Asp Ala Thr Lys Thr Phe Thr Val Thr Glu
65                  70                  75

<210> SEQ ID NO 7
<211> LENGTH: 502
<212> TYPE: PRT
<213> ORGANISM: Artificial Sequence
```

<220> FEATURE:
<223> OTHER INFORMATION: amino acid sequence of N-terminal MBP fused RA

<400> SEQUENCE: 7

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Ser Gly Gly Gly Gly Met Phe Asp Ala Ser Asn Phe Lys Asp Phe Ser
    370                 375                 380

Ser Ile Ala Ser Ala Ser Ser Ser Trp Gln Asn Gln Ser Gly Ser Thr
385                 390                 395                 400
```

```
Met Ile Ile Gln Val Asp Ser Phe Gly Asn Val Ser Gly Gln Tyr Val
            405                 410                 415

Asn Arg Ala Gln Gly Thr Gly Cys Gln Asn Ser Pro Tyr Pro Leu Thr
            420                 425                 430

Gly Arg Val Asn Gly Thr Phe Ile Ala Phe Ser Val Gly Trp Asn Asn
            435                 440                 445

Ser Thr Glu Asn Cys Asn Ser Ala Thr Gly Trp Thr Gly Tyr Ala Gln
            450                 455                 460

Val Asn Gly Asn Asn Thr Glu Ile Val Thr Ser Trp Asn Leu Ala Tyr
465                 470                 475                 480

Glu Gly Gly Ser Gly Pro Ala Ile Glu Gln Gly Gln Asp Thr Phe Gln
            485                 490                 495

Tyr Val Pro Thr Thr Glu
            500
```

<210> SEQ ID NO 8
<211> LENGTH: 502
<212> TYPE: PRT
<213> ORGANISM: Artificial Sequence
<220> FEATURE:
<223> OTHER INFORMATION: amino acid sequence of N-terminal MBP fused mRA

<400> SEQUENCE: 8

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
            85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
            165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255
```

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Ser Gly Gly Gly Met Phe Asp Ala Ser Asn Phe Lys Asp Phe Ser
    370                 375                 380

Ser Ile Ala Ser Ala Ser Ser Trp Gln Asn Gln Ser Gly Ser Thr
385                 390                 395                 400

Met Ile Ile Gln Val Asp Ser Phe Gly Asn Val Ser Gly Gln Tyr Val
                405                 410                 415

Asn Arg Ala Gln Gly Thr Gly Cys Gln Asn Ser Pro Tyr Pro Leu Thr
            420                 425                 430

Gly Arg Val Asn Gly Thr Phe Ile Asp Phe Ser Val Lys Trp Asn Asn
        435                 440                 445

Ser Thr Glu Asn Cys Asn Ser Asn Thr Gln Trp Thr Gly Tyr Ala Gln
    450                 455                 460

Val Asn Gly Asn Thr Glu Ile Val Thr Arg Trp Asn Leu Lys Tyr
465                 470                 475                 480

Glu Gly Gly Ser Gly Pro Ala Ile Glu Gln Gly Gln Asp Thr Phe Gln
                485                 490                 495

Tyr Val Pro Thr Thr Glu
            500

<210> SEQ ID NO 9
<211> LENGTH: 502
<212> TYPE: PRT
<213> ORGANISM: Artificial Sequence
<220> FEATURE:
<223> OTHER INFORMATION: amino acid sequence of N-terminal MBP fused MA

<400> SEQUENCE: 9

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
    355                 360                 365

Ser Gly Gly Gly Gly Met Phe Asp Ala Ser Asn Phe Lys Asp Phe Ser
370                 375                 380

Ser Ile Ala Ser Ala Ser Ser Ser Trp Gln Asn Gln His Gly Ser Thr
385                 390                 395                 400

Met Ile Ile Gln Val Asp Ser Phe Gly Asn Val Ser Gly Gln Tyr Val
                405                 410                 415

Asn Arg Ala Glu Gly Thr Gly Cys Gln Asn Ser Pro Tyr Pro Leu Thr
            420                 425                 430

Gly Arg Val Asn Gly Thr Phe Ile Asp Phe Ser Val Lys Trp Asn Asn
    435                 440                 445

Ser Thr Glu Asn Cys Asn Ser Asn Thr Gln Trp Thr Gly Tyr Ala Gln
450                 455                 460

Val Asn Gly Asn Asn Thr Glu Ile Val Thr Arg Trp Asn Leu Lys Tyr
465                 470                 475                 480

Glu Gly Gly Ser Gly Pro Ala Ile Trp Gln Gly Gln Asp Thr Phe Gln
                485                 490                 495

Tyr Val Pro Thr Thr Glu
            500

<210> SEQ ID NO 10
<211> LENGTH: 465

-continued

<212> TYPE: PRT
<213> ORGANISM: Artificial Sequence
<220> FEATURE:
<223> OTHER INFORMATION: amino acid sequence of MA-Ft

<400> SEQUENCE: 10

```
Met Phe Asp Ala Ser Asn Phe Lys Asp Phe Ser Ser Ile Ala Ser Ala
1               5                   10                  15

Ser Ser Ser Trp Gln Asn Gln His Gly Ser Thr Met Ile Ile Gln Val
            20                  25                  30

Asp Ser Phe Gly Asn Val Ser Gly Gln Tyr Val Asn Arg Ala Glu Gly
        35                  40                  45

Thr Gly Cys Gln Asn Ser Pro Tyr Pro Leu Thr Gly Arg Val Asn Gly
    50                  55                  60

Thr Phe Ile Asp Phe Ser Val Lys Trp Asn Asn Ser Thr Glu Asn Cys
65                  70                  75                  80

Asn Ser Asn Thr Gln Trp Thr Gly Tyr Ala Gln Val Asn Gly Asn Asn
                85                  90                  95

Thr Glu Ile Val Thr Arg Trp Asn Leu Lys Tyr Glu Gly Gly Ser Gly
            100                 105                 110

Pro Ala Ile Trp Gln Gly Gln Asp Thr Phe Gln Tyr Val Pro Thr Thr
        115                 120                 125

Glu Ala Glu Ala Ala Ala Lys Glu Ala Ala Ala Lys Glu Ala Ala Ala
    130                 135                 140

Lys Ala Thr Tyr Lys Leu Val Ile Asn Gly Lys Thr Leu Lys Gly Glu
145                 150                 155                 160

Thr Thr Thr Lys Ala Val Asp Ala Glu Thr Ala Glu Lys Ala Phe Lys
                165                 170                 175

Gln Tyr Ala Asn Asp Tyr Gly Val Asp Gly Val Trp Thr Tyr Asp Asp
            180                 185                 190

Ala Thr Lys Thr Phe Thr Val Thr Glu Lys Pro Glu Val Ile Asp Ala
        195                 200                 205

Ser Glu Leu Thr Pro Ala Val Thr Thr Tyr Lys Leu Val Ile Asn Gly
    210                 215                 220

Lys Thr Leu Lys Gly Glu Thr Thr Thr Lys Ala Val Asp Ala Glu Thr
225                 230                 235                 240

Ala Glu Lys Ala Phe Lys Gln Tyr Ala Asn Asp Tyr Gly Val Asp Gly
                245                 250                 255

Val Trp Thr Tyr Asp Asp Ala Thr Lys Thr Phe Thr Val Thr Glu Gly
            260                 265                 270

Gly Gly Gly Ser Gly Ser Gly Gly Gly Gly Met Thr Thr Ala Ser Thr
        275                 280                 285

Ser Gln Val Arg Gln Asn Tyr His Gln Asp Ser Glu Ala Ala Ile Asn
    290                 295                 300

Arg Gln Ile Asn Leu Glu Leu Tyr Ala Ser Tyr Val Tyr Leu Ser Met
305                 310                 315                 320

Ser Tyr Tyr Phe Asp Arg Asp Asp Val Ala Leu Lys Asn Phe Ala Lys
                325                 330                 335

Tyr Phe Leu His Gln Ser His Glu Glu Arg Glu His Ala Glu Lys Leu
            340                 345                 350

Met Lys Leu Gln Asn Gln Arg Gly Gly Arg Ile Phe Leu Gln Asp Ile
        355                 360                 365

Lys Lys Pro Asp Cys Asp Asp Trp Glu Ser Gly Leu Asn Ala Met Glu
    370                 375                 380
```

-continued

| Cys 385 | Ala | Leu | His | Leu 390 | Glu | Lys | Asn | Val | Asn 395 | Gln | Ser | Leu | Leu | Glu 400 | Leu |
| His | Lys | Leu | Ala | Thr 405 | Asp | Lys | Asn | Asp | Pro 410 | His | Leu | Cys | Asp | Phe 415 | Ile |
| Glu | Thr | His | Tyr 420 | Leu | Asn | Glu | Gln | Val 425 | Lys | Ala | Ile | Lys | Glu 430 | Leu | Gly |
| Asp | His | Val 435 | Thr | Asn | Leu | Arg | Lys 440 | Met | Gly | Ala | Pro | Glu 445 | Ser | Gly | Leu |
| Ala | Glu 450 | Tyr | Leu | Phe | Asp | Lys 455 | His | Thr | Leu | Gly | Asp 460 | Ser | Asp | Asn | Glu |
| Ser 465 | | | | | | | | | | | | | | | |

MONOMERIC AVIDIN-LIKE PROTEINS WITH STABLE BIOTIN BINDING ABILITY

CROSS-REFERENCE TO RELATED APPLICATIONS

This application claims priority from Korean Patent Application No. 10-2015-0148989, filed on Oct. 26, 2015 in the Korean Intellectual Property Office, the disclosure of which is incorporated herein by reference in its entirety.

FIELD

The present disclosure relates to monomeric avidin-like proteins with a strong and stable biotin-binding ability, protein conjugates containing two or more of the monomeric avidin-like proteins and having a multivalent binding ability to biotin, nucleic acid molecules for encoding the monomeric avidin-like proteins, and methods for producing the monomeric avidin-like proteins.

BACKGROUND

Streptavidin (STA) and avidin proteins are homotetramers that have extraordinarily high binding affinities for the small molecule biotin ($K_d$~$10^{-14}$ M)[1]. This remarkably strong and specific interaction between streptavidin or avidin and biotin has been exploited in a wide range of applications, such as bio-interfaces to nanostructure assembly and molecular labeling [2]. The tetrameric form of avidin proteins, however, may cause unwanted cross-linking of the biotin conjugates. For example, streptavidin-based labeling of biotinylated cell-surface receptors disrupted the normal function of the receptors through oligomerization [3]. However, the development of monomeric streptavidin or avidin without a dramatic decrease ($K_d$~$10^{-7}$-$10^{-9}$ M) in biotin affinity has not been successful because a tryptophan residue from an adjacent subunit is critical for strong biotin binding [4-7]. Instead, a tetrameric but monovalent streptavidin with a single biotin binding site was developed [3]. Although this monovalent streptavidin is very effective for biotin labeling without cross-linking [8], a truly monomeric streptavidin or avidin protein is still highly desired for minimal perturbation of biotin-labeled targets and even more diverse applications of avidin proteins. For example, monomeric avidin can be genetically fused with other target proteins without oligomerization, and this fusion will also allow a new form of creation having different spatial organization and valency of the biotin binding sites.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

SUMMARY

The present inventors researched and endeavored to develop monomeric avidin. As a result, the present inventors monomerized rhizavidin by introducing a mutation at the interface of monomers of dimeric rhizavidin, which is one of the avidin proteins, and further improved the binding stability with biotin by further introducing additional amino acid alterations to the obtained monomeric avidin, and thus have completed the present invention.

An aspect of the present invention is to provide monomeric avidin-like proteins having a strong and stable biotin-binding ability.

Another aspect of the present invention is to provide protein conjugates containing two or more of the monomeric avidin-like proteins and having a multivalent binding ability to biotin.

Still another aspect of the present invention is to provide nucleic acid molecules for encoding the monomeric avidin-like proteins.

Still another aspect of the present invention is to provide methods for producing the monomeric avidin-like proteins and the protein conjugates having a multivalent binding ability to biotin.

Other purposes and advantages of the present disclosure will become more obvious with the following detailed description of the invention, claims, and drawings.

In order to accomplish these objects, there is provided a monomeric avidin-like protein with a strong and stable biotin-binding ability, including an amino acid sequence in which the $67^{th}$, $71^{st}$, $82^{nd}$, $84^{th}$, $101^{st}$, and $105^{th}$ amino acid residues of SEQ ID NO: 1 are substituted with charged and hydrophilic amino acids, wherein the charged and hydrophilic amino acids are selected from the group consisting of aspartic acid, lysine, asparagine, glutamine, and arginine.

The present inventors researched and endeavored to develop monomeric avidin. As a result, the present inventors monomerized rhizavidin by introducing a mutation at the interface of monomers of dimeric rhizavidin, which is one of the avidin proteins, and further improved the binding stability with biotin by further introducing additional amino acid alterations to the obtained monomeric avidin.

As used herein, the term "monomeric avidin-like protein" is used to underline having a monomeric form thereof that is differentiated from existing avidin proteins in view of the form, while it has a biotin-binding ability, like avidin proteins. In addition, herein, the term "monomeric avidin-like protein" is used together with the term "monodin" or "monomeric avidin".

The monomeric avidin-like protein of the present invention basically includes the amino acid sequence of SEQ ID NO: 1, wherein $67^{th}$ (alanine), $71^{st}$ (glycine), $82^{nd}$ (alanine), $84^{th}$ (glycine), $101^{st}$ (serine), and $105^{th}$ (alanine) amino acid residues are substituted with charged and hydrophilic amino acids. The substitution of amino acid residues at these sites is an important factor in producing monomeric avidin proteins having a biotin-binding ability.

According to an embodiment of the present invention, SEQ ID NO: 1 is an amino acid sequence derived from a monomer constituting rhizavidin, which is a dimeric avidin protein. Rhizavidin is the first naturally occurring dimer in the avidin protein family with a high binding affinity for biotin. SEQ ID NO: 1 is a sequence in a truncated form in which some sequences at the N-termini and C-termini are removed from the full-length of a monomer constituting rhizavidin.

According to an embodiment of the present invention, the monomeric avidin-like protein of the present invention includes the amino acid sequence of SEQ ID NO: 2. SEQ ID NO: 2 is a sequence in which the $67^{th}$ (alanine), $71^{st}$ (glycine), $82^{nd}$ (alanine), $84^{th}$ (glycine), $101^{st}$ (serine), and $105^{th}$ (alanine) amino acid residues of SEQ ID NO: 1 are substituted with aspartic acid, lysine, asparagine, glutamine, arginine, and lysine, respectively.

The monomeric avidin-like protein of the protein may have an additional amino acid substitution in order to further improve the binding stability with biotin.

According to an embodiment, the monomeric avidin-like protein of the present invention includes an amino acid sequence in which the $23^{rd}$ (serine), $46^{th}$ (glutamine), and $115^{th}$ (glutamic acid) amino acid residues of SEQ ID NO: 1 are further substituted with amino acids selected from the group consisting of histidine, glutamic acid, and tryptophan.

According to a more specific embodiment of the present invention, the monomeric avidin-like protein of the present invention includes the amino acid sequence of SEQ ID NO: 3. SEQ ID NO: 3 is a sequence in which $23^{rd}$ (serine), $46^{th}$ (glutamine), and $115^{th}$ (glutamic acid) amino acid residues of SEQ ID NO: 2 are substituted with histidine, glutamic acid, and tryptophan, respectively. The monomeric avidin-like protein of SEQ ID NO: 3 is described under the name of monodin in examples below, and as confirmed in the examples, although it has a monomeric form, the biotin-binding stability thereof was almost as stable as tetrameric streptavidin.

According to an embodiment, with respect to the binding affinity to a biotin conjugate, the monomeric avidin-like protein has an off-rate of $0.5 \times 10^{-5}$ $s^{-1}$ to $7.0 \times 10^{-5}$ $s^{-1}$. In a specific embodiment, the off-rate is $0.6 \times 10^{-5}$ $s^{-1}$ to $7.0 \times 10^{-5}$ $s^{-1}$, $0.7 \times 10^{-5}$ $s^{-1}$ to $7.0 \times 10^{-5}$ $s^{-1}$, $0.8 \times 10^{-5}$ $s^{1}$ to $7.0 \times 10^{-5}$ $s^{1}$, $0.9 \times 10^{-5}$ $s^{-1}$ to $7.0 \times 10^{-5}$ $s^{-1}$, or $1.0 \times 10^{-5}$ $s^{-1}$ to $7.0 \times 10^{-5}$ $s^{-1}$.

The off-rate may be measured at a temperature of 23-45° C.

According to a more specific embodiment, the off-rate 23° C. is $1.0 \times 10^{-5}$ $s^{-1}$ or smaller (e.g., $0.5 \times 10^{-5}$ $s^{-1}$ to $1.0 \times 10^{-5}$ $s^{-1}$, $0.6 \times 10^{-5}$ $s^{-1}$ to $1.0 \times 10^{-5}$ $s^{-1}$, $0.7 \times 10^{-5}$ $s^{-1}$ to $1.0 \times 10^{-5}$ $s^{-1}$, $0.8 \times 10^{-5}$ $s^{-1}$ to $1.0 \times 10^{-5}$ $s^{-1}$, or $0.9 \times 10^{-5}$ $s^{-1}$ to $1.0 \times 10^{-5}$ $s^{-1}$) when measured at 23° C.; $6.0 \times 10^{-5}$ $s^{-1}$ to $6.7 \times 10^{-5}$ $s^{-1}$ at 45° C., and $2.0 \times 10^{-5}$ $s^{-1}$ to $6.2 \times 10^{-5}$ $s^{-1}$ at 37° C.

According to an embodiment of the present invention, the biotin conjugate is a conjugate of biotin and a protein, a conjugate of biotin and a peptide, or a conjugate of biotin and a nucleic acid.

The sequences of the monomeric avidin-like protein described herein and biological equivalents thereof, so long as they can bind to biotin, may be included in the scope of the present invention. For example, in order to further improve binding affinity and/or other biological characteristics of the avidin-like protein, the amino acid sequence thereof may be additionally altered. Such alterations include, for example, deletion, insertion, and/or substitution of amino acid residues in the amino acid sequence of the avidin-like protein. Such amino acid mutations are based on the relative similarity of the amino acid side-chain substituents, for example, their hydrophobicity, hydrophilicity, charge, size, or the like. An analysis of the size, shape, and type of the amino acid side-chain substituents may reveal that: arginine, lysine, and histidine are all positively charged residues; alanine, glycine, and serine are similar in size; and phenylalanine, tryptophan, and tyrosine are similar in shape. Therefore, on the basis of these considerations, arginine, lysine, and histidine; alanine, glycine, and serine; and phenylalanine, tryptophan, and tyrosine may be considered to be biologically functional equivalents.

For introducing mutations, hydropathy indexes of amino acids may be considered. Each amino acid residue has been assigned a hydropathic index on the basis of its hydrophobicity and charge characteristics: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

Meanwhile, it is also well known that the substitution between amino acids with similar hydrophilicity values results in proteins having equivalent biological activity. As disclosed in U.S. Pat. No. 4,554,101, each amino acid residue has been assigned the following hydrophilicity values: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Amino acid exchanges in the protein, which do not generally alter the molecular activity, are known in the art (H. Neurath, R. L. Hill, The Proteins, Academic Press, New York, 1979). The most commonly occurring exchanges are changes between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

Considering the foregoing mutations with the biological equivalent activity, the avidin-like protein of the present invention is construed to also include sequences having substantial identity to the sequences set forth in the sequence listings. The substantial identity means that, when the sequence of the present invention and another optional sequence are aligned to correspond to each other as much as possible and the aligned sequences are analyzed using an algorithm normally used in the art, the corresponding sequences have at least 61%, more preferably at least 70%, still more preferably at least 80%, and most preferably at least 90% sequence identity. Methods of alignment for sequence comparison are known in the art. Various methods and algorithms for alignment are disclosed in Smith and Waterman, *Adv. Appl. Math.* (1981) 2:482; Needleman and Wunsch, *J. Mol. Bio.* (1970) 48:443; Pearson and Lipman, *Methods in Mol. Biol.* (1988) 24: 307-31; Higgins and Sharp, *Gene* (1988) 73:237-44; Higgins and Sharp, *CABIOS* (1989) 5:151-3; Corpet et al., *Nuc. Acids Res.* (1988) 16:10881-90; Huang et al., *Comp. Appl. BioSci.* (1992) 8:155-65 and Pearson et al., *Meth. Mol. Biol.* (1994) 24:307-31. The NCBI Basic Local Alignment Search Tool (BLAST, Altschul et al., *J. Mol. Biol.* (1990) 215:403-10) is available from the NCBI, and on the Internet, for use in connection with the sequence analysis programs blastp, blasm, blastx, tblastn, and tblastx. BLAST can be accessed at www.ncbi.nlm.nih.gov/BLAST/. A description of how to determine sequence identity using this program is available at www.ncbi.nlm.nih.gov/BI-AST/blast_help.html.

In accordance with another aspect of the present invention, there is provided a protein conjugate including: a multimeric protein; and two or more of the monomeric avidin-like proteins, the protein conjugate having a multivalent binding ability to biotin.

As used herein, the "multimeric protein" refers to a molecule protein of some monomers bound together or a molecule protein composed of two or more polypeptide chains. The monovalent monomeric avidin-like protein of the present invention is bound to each monomer or polypeptide sequence constituting the multimeric protein to obtain a protein conjugate having a multivalent binding ability to biotin.

According to an embodiment, the multimeric protein is 24-meric ferritin.

In accordance with still another aspect of the present invention, there is provided a nucleic acid molecule for encoding the monomeric avidin-like protein.

As used herein, the term "nucleic acid molecule" refers to comprehensively including DNA (gDNA and cDNA) and RNA molecules, and the nucleotide as a basic component unit in the nucleic acid molecule includes naturally occurring nucleotides and analogues with modified sugars or bases (Scheit, Nucleotide Analogs, John Wiley, New York (1980); Uhlman, and Peyman, *Chemical Reviews*, 90:543-584(1990)).

The sequence of the nucleic acid molecule for encoding the monomeric avidin-like protein of the present invention may be altered. The alteration includes addition, deletion, or non-conservative substitution or conservative substitution of nucleotides.

In accordance with still another aspect of the present invention, there is provided a method for producing a monomeric avidin-like protein with a biotin binding ability, the method including:

(a) transforming a host cell with a recombinant vector comprising the nucleic acid of claim 11; and (b) culturing the transformant to express a monomeric avidin-like protein having a biotin binding ability.

As used herein, the term "vector" refers to any vehicle that is used to express a target gene in a host cell, and encompasses: plasmid vectors; cosmid vectors; and viral vectors, such as bacteriophage vectors, adenoviral vectors, retroviral vectors, and adeno-associated viral vectors.

In the recombinant vector, the nucleic acid molecule for encoding the monomeric avidin-like protein is operatively linked to a promoter. The term "operatively linked" refers to a functional linkage between a nucleic acid expression regulatory sequence (e.g., a promoter, a signal sequence, or an array of transcriptional regulatory factor binding sites) and another nucleic acid sequence, and the regulatory sequence thus regulates the transcription and/or translation of the other nucleic acid sequence.

The recombinant vector system may be constructed by various methods that are known in the art, and a specific method therefor is disclosed in Sambrook et al., *Molecular Cloning, A Laboratory Manual*, Cold Spring Harbor Laboratory Press (2001), which is incorporated herein by reference.

The recombinant vector may be constructed by employing eukaryotic cells or prokaryotic cells as host cells. In cases where the recombinant vector is an expression vector and employs a prokaryotic cell as a host cell, it generally includes strong promoters to initiate transcription (e.g., tac promoter, lac promoter, lacUV5 promoter, lpp promoter, $p_L^\lambda$ promoter, $p_R^\lambda$ promoter, racy promoter, amp promoter, recA promoter, SP6 promoter, trp promoter, and T7 promoter), a ribosome binding site for translation initiation, and transcription/translation termination sequences. In cases where *E. coli* (e.g., HB101, BL21, DH5α etc.) is used as a host cell, the promoter and operator regions for the *E. coli* tryptophan biosynthesis pathway (Yanofsky, C., *J. Bacteriol.*, (1984) 158:1018-1024) and the leftward promoter from phage λ ($p_L\lambda$ promoter, Herskowitz, I. and Hagen, D., *Ann. Rev. Genet.*, (1980) 14:399-445) may be used as a regulatory region. *Bacillus* as the host cell may use the promoter of a toxic protein gene of *Bacillus thuringiensis* (*Appl. Environ. Microbiol.* (1998) 64:3932-3938; *Mol. Gen. Genet.* (1996) 250:734-741) or any promoter that can be expressed in *Bacillus*, as the regulatory region.

The recombinant vector may be constructed by manipulating a plasmid (e.g.: pCL, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (e.g.,: λgt4.λB, λ-Charon, λΔz1, M13, etc.) or a virus (e.g.,: SV40, etc.) that is commonly used in the art.

On the other hand, in cases where the recombinant vector is an expression vector, and employs an eukaryotic cell as a host cell, the recombinant may employ a promoter derived from the genome of mammalian cells (e.g., metallothionein promoter, β-actin promoter, human hemoglobin promoter, and human muscle creatine promoter) or a promoter derived from mammalian viruses (e.g., adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of moloney virus, Epstein barr virus (EBV) promoter and Rous sarcoma virus (RSV) promoter), and may typically have a polyadenylated sequence as the transcription termination sequence.

The recombinant vector may be fused with the other sequences to facilitate the purification of the proteins expressed therefrom. Examples of the fusion sequence include, for example, glutathione S-transferase (Pharmacia, USA), maltose binding protein (NEB, USA), FLAG (IBI, USA), and 6× His (hexahistidine; Quiagen, USA).

Any host cell that is known in the art may be used as a host cell capable of stably and continuously cloning and expressing the recombinant vector, and examples thereof may include prokaryotic host cells, for example, *Escherichia coli*, *Bacillus* sp. strains, such as *Bacillus subtilis* and *Bacillus thuringiensis*, *Streptomyces*, *Pseudomonas* (e.g., *Pseudomonas putida*), *Proteus mirabilis* or *Staphylococcus* (e.g., *Staphylocus carnosus*).

Suitable eukaryotic cells for the recombinant vector may include fungus (such as *Aspergillus* species), yeasts (such as *Pichia pastoris*, *Saccharomyces cerevisiae*, *Schizosaccharomyces*, and *Neurospora crassa*), the other lower eukaryotic cells, cells of higher eukaryotes, such as insect-derived cells, and cells derived from plants or mammals.

As used herein, the "transformation" into host cells include any method by which nucleic acids are introduced into organism, cells, tissues, or organs, and as known in the art, suitable standard techniques according to host cells may be selected and performed. Examples of the techniques may include electroporation, protoplast fusion, calcium phosphate (CaPO4) precipitation, calcium chloride ($CaCl_2$) precipitation, agitation using silicon carbide fibers, agrobacteria-mediated transformation, PEG, dextran sulfate, lipofectamine, and drying/inhibition-mediated transformation, but are not limited thereto.

In step (b), the transformed host cells may be cultured in a suitable media known in the art according to culturing conditions. The culture procedure can be easily manipulated according to the selected strain by a person skilled in the art. Various culture methods are disclosed in various literatures (e.g., James M. Lee, *Biochemical Engineering*, Prentice-Hall International Editions, 138-176). Cell culture methods are divided into suspension and adhesion culture according to the cell growth manner; and batch culture, fed-batch culture, and continuous culture according to the culturing method. The media used in the culture need to appropriately satisfy requirements for particular strains.

The proteins obtained by culturing transformed host cells may be used in an unpurified condition, and may be purified at high purity, before use, by various normal methods, for example, dialysis, salt precipitation, and chromatography. Of these, the purification using chromatography is most frequently employed, and the kind and order of columns may be selected from ion-exchange chromatography, size-exclusion chromatography, affinity chromatography, and the like, according to the characteristics of protein, culturing method, and so on.

Features and advantages of the present invention are summarized as follows:

(i) The present invention provides monomeric avidin-like proteins with a strong and stable biotin-binding ability, protein conjugates containing two or more of the monomeric avidin-like proteins and having a multivalent binding ability to biotin, nucleic acid molecules for encoding the monomeric avidin-like proteins, and methods for producing the monomeric avidin-like proteins.

(ii) The present invention, due to the monomeric structure, is free from a problem of the disruption of receptor functions, caused by oligomerization occurring in existing tetrameric streptavidin or tetrameric but monovalent streptavidin variants.

(iii) The present invention can be used to prepare a high-valent avidin probe, and this avidin probe can be used to diversify the avidin/biotin binding strategy for constructing novel bio-structures and nano-structures.

BRIEF DESCRIPTION OF THE DRAWINGS

The above and other objects, features, and advantages of the present invention will be more apparent from the following detailed description taken in conjunction with the accompanying drawings.

The monomeric protein with a single mutation (1M: S69R) was very unstable and readily aggregated in buffered solutions because many hydrophobic residues at the dimeric interface are exposed to the solution. On the other hand, more heavily mutated monomers (mRA and 10 M) were stable without any aggregation (up to 1 mg/ml). As shown in (b) of FIG. 5, upon incubation with excess free biotin, the dissociation from biotin-GFP, of the monomeric variant (10 M) with ten mutation residues, was faster than that of the monomer (mRA) with six mutations.

Figure 6:
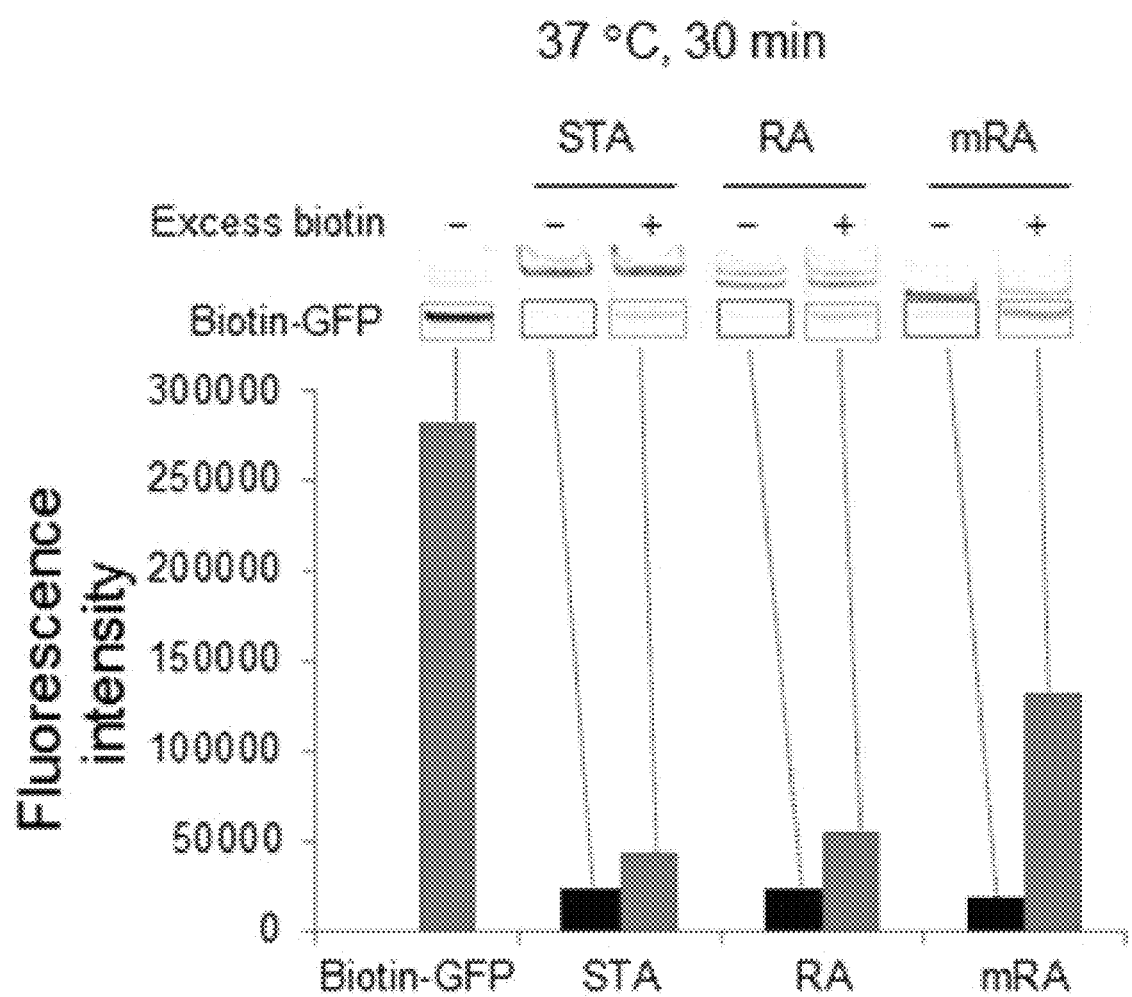

FIG. 6 illustrates biotin binding stability of streptavidin (STA), rhizavidin (RA), and monomeric rhizavidin (mRA). Tetrameric STA, dimeric RA, and monomeric mRA were mixed with biotin-GFP, and the dissociation of biotin-GFP from avidin proteins under excess free biotin conditions were checked by native-PAGE analysis (at 37° C. for 30 min). The degrees of biotin-GFP dissociated from avidin proteins before (black) and after (red) the biotin addition were measured from background-calibrated intensities of free biotin-GFP bands on a fluorescence image. Over 40% of biotin-GFP was dissociated from mRA, while less than 20% of biotin-GFP was dissociated from multimeric STA or RA.

Figure 7:
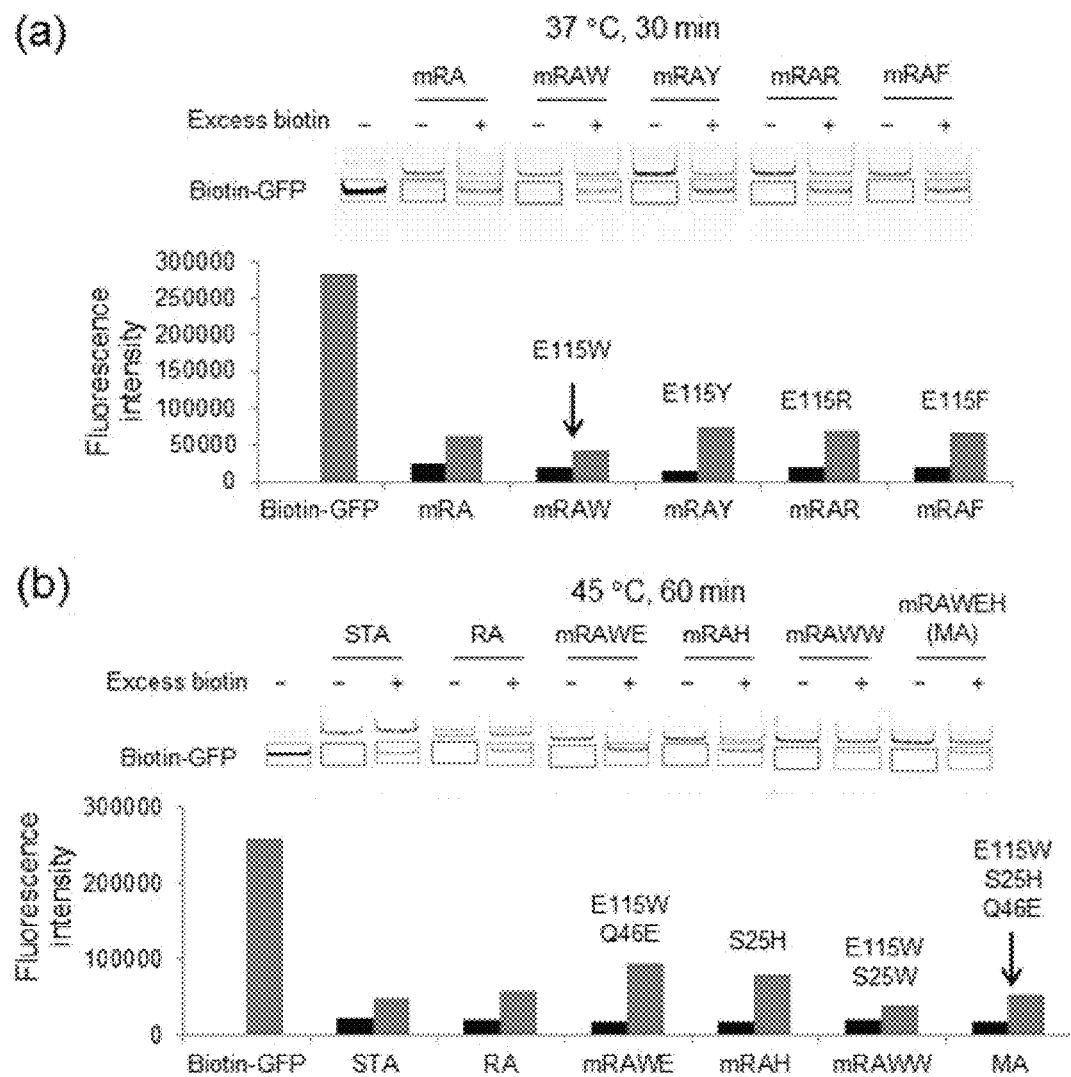

FIG. 7 illustrates biotin binding stability of monomeric rhizavidin (mRA) variants. (a) The degrees of biotin-GFP dissociated from mRA mutants at E115 before (black) and after (red) the biotin addition (at 37° C. for 30 min). (a) The degrees of biotin-GFP dissociated from mRA mutants at E115, Q46, and S23 before (black) and after (red) the biotin addition (at 45° C. for 30 min). Selected mutations with optimally slowed off-rates from biotin-GFP were indicated with arrows. Although mRA with two tryptophan mutations (E115W and S23W) showed the least dissociation of biotin-GFP, mRAWW was highly prone to aggregation.

Figure 8:
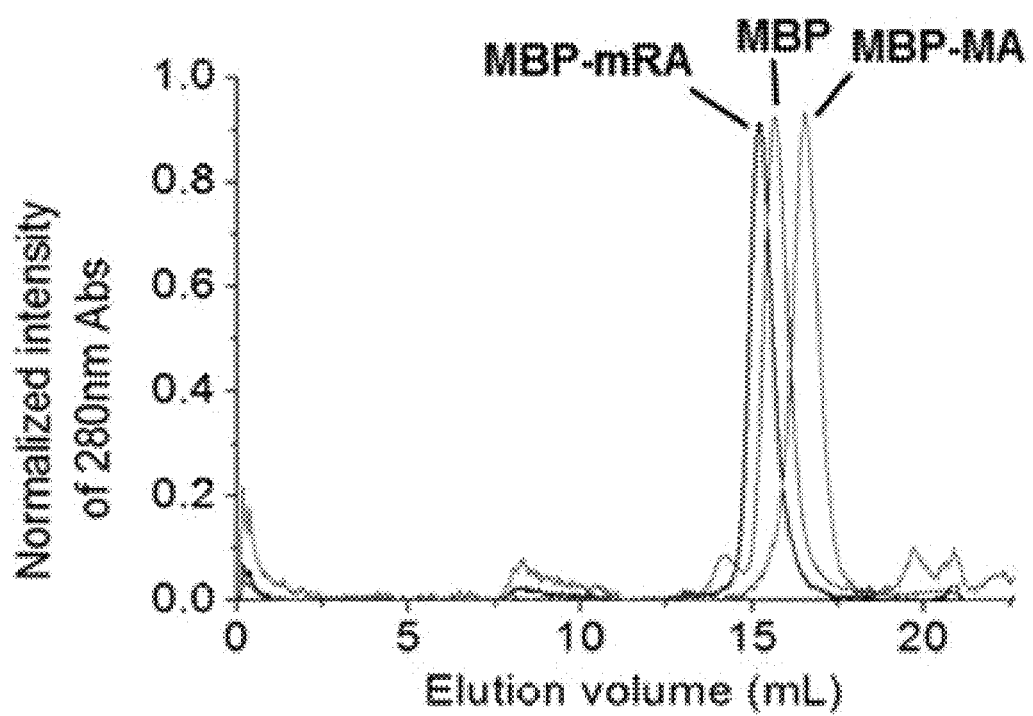

FIG. 8 illustrates size exclusion chromatography of MBP and MBP-fused monomeric rhizavidin (mRA), and MBP-fused monodin (MA). Monodin slightly delayed an elution time due to the mutated surface residues (E115W, S23H, and Q46E).

Figure 9:
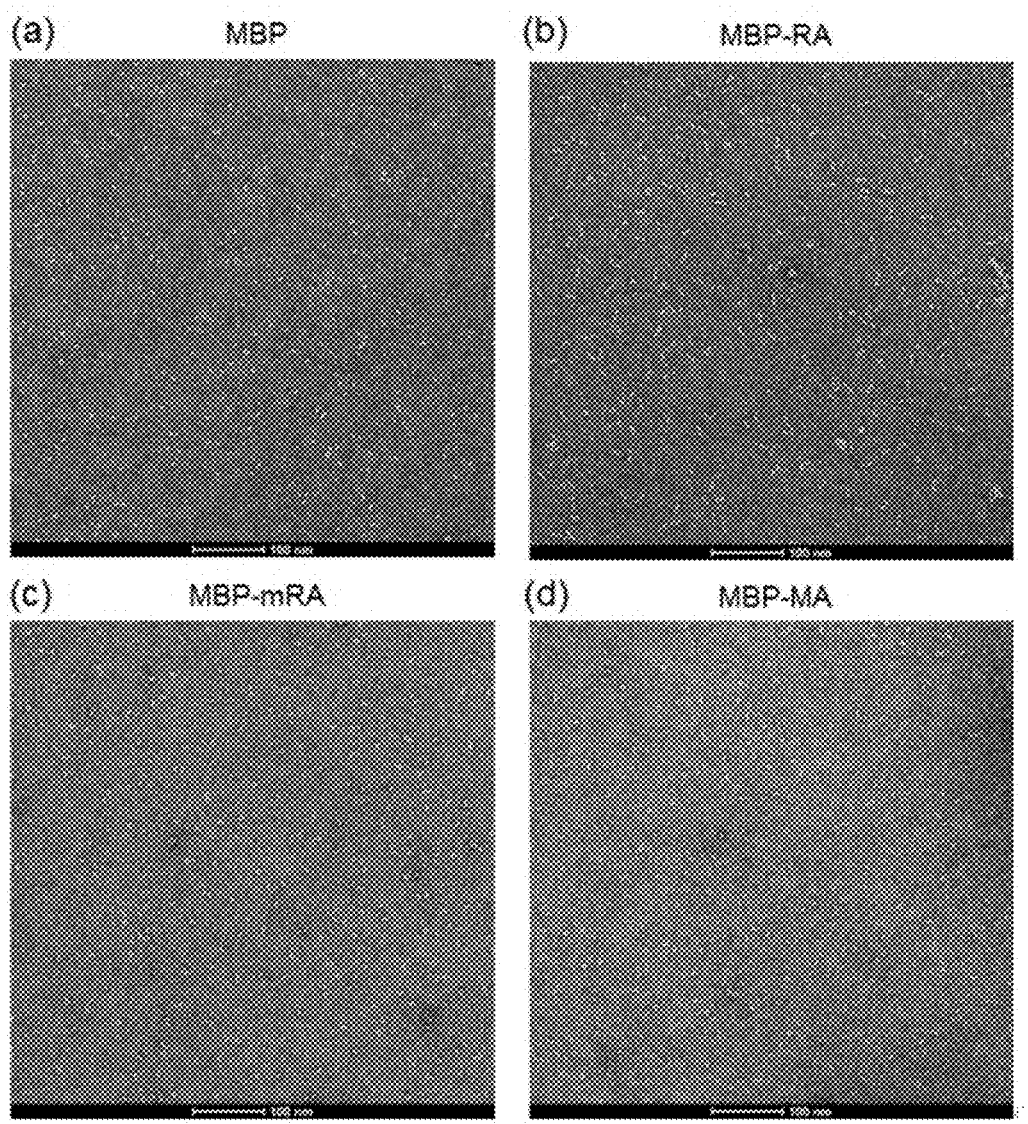
Figure 10:
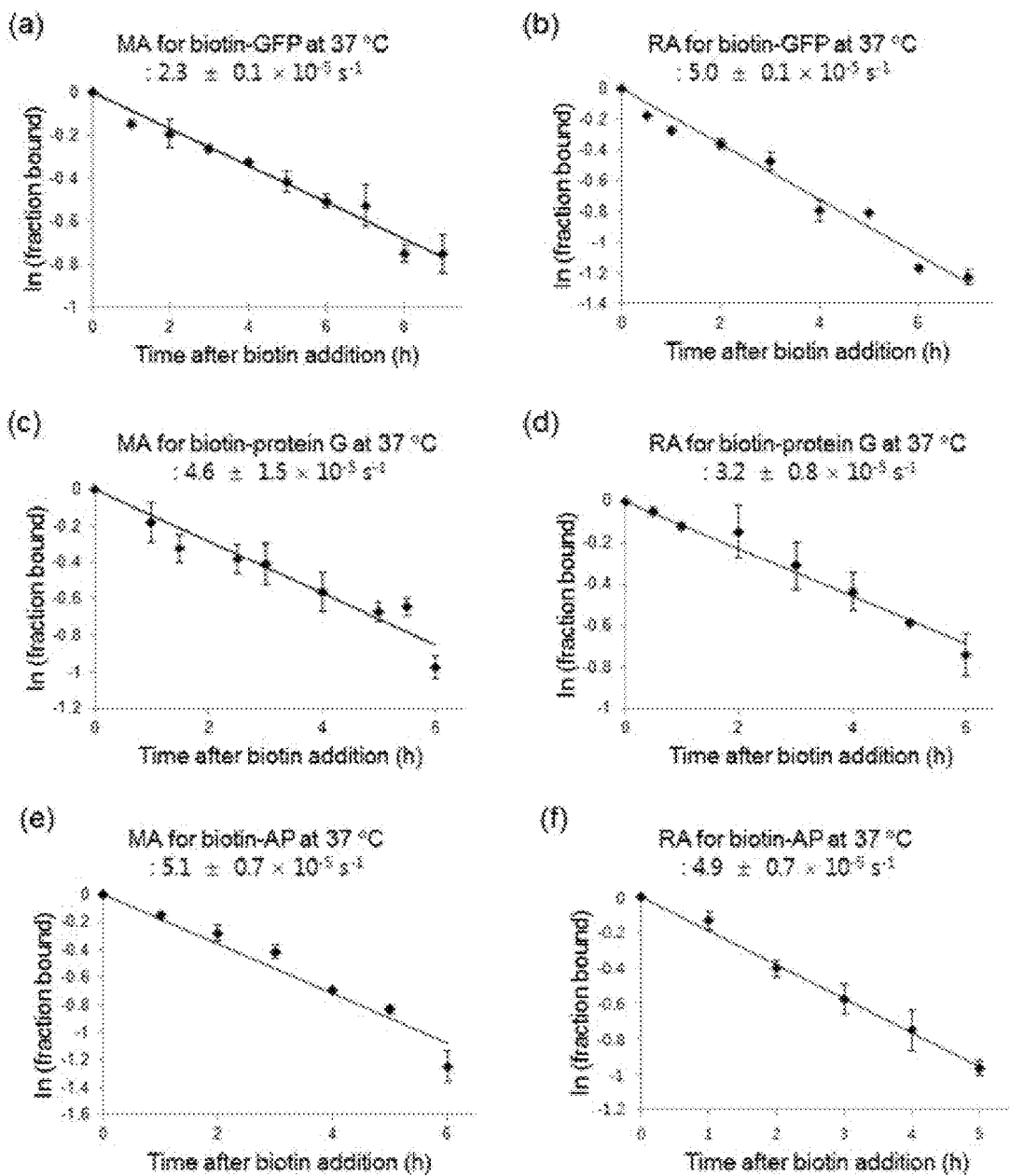

FIG. 9 illustrates TEM images of (a) MBP as well as MBP fused with (b) dimeric rhizavidin (RA), (c) monomeric rhizavidin (mRA), or (d) monodin (MA). Scale bars: 100 nm FIG. 10 illustrates dissociation rates of monodin (MA) and rhizavidin (RA) from protein-based biotin conjugates. In addition to biotin-GFP, the site-specific biotinylation peptide (AP) was also fused to relatively small (~12 kDa) protein G (biotin-protein G). The AP-peptide with a fluorescent dye (biotin-AP) was also synthesized. These protein (or peptide)-based biotin conjugates showed similar binding stability to MA and RA (off-rates: $2\text{-}5 \times 10^{-5}$ $s^{-1}$).

Figure 11:
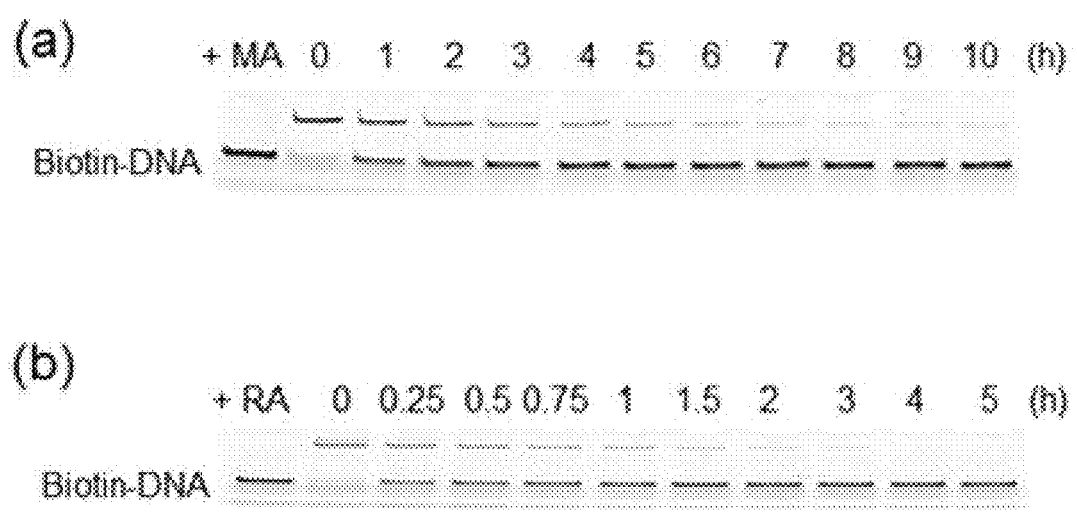

FIG. 11 illustrates native gel analysis to determine dissociation rates of (a) monodin (MA) and (b) rhizavidin (RA) from biotin-DNA at 37° C.

Figure 12:
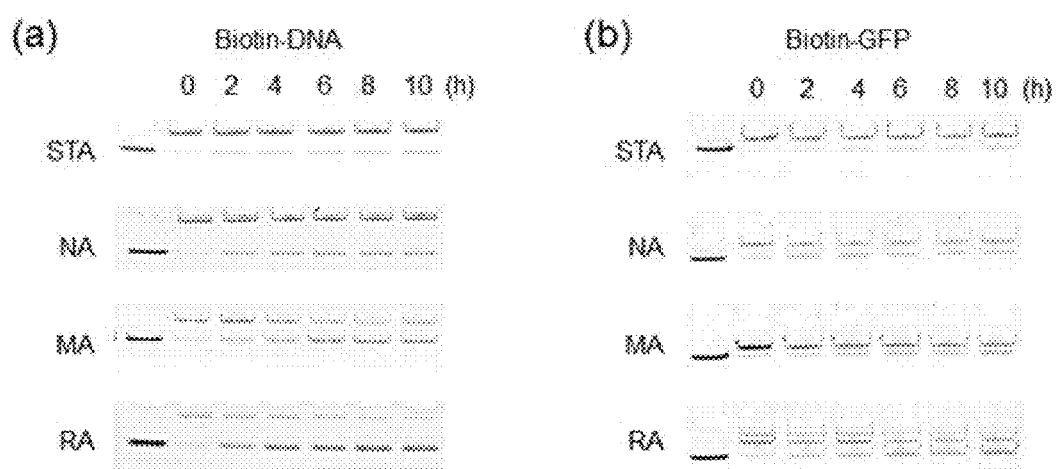

FIG. 12 illustrates native gel analysis to determine dissociation rates of streptavidin (STA), neutravidin (NA), monodin (MA), and rhizavidin (RA) from (a) biotin-DNA or (b) biotin-GFP at 23° C. Off-rates (summarized in Table S1) were examined by monitoring increased band intensities of dissociated free biotin conjugates. Complex formation with avidin proteins altered fluorescence signals of biotin conjugates in native gels. For example, fluorescence band intensities of biotin-DNA-fluorescein were significantly quenched by complex formation with RA, and a lesser degree with NA or MA.

Figure 13:
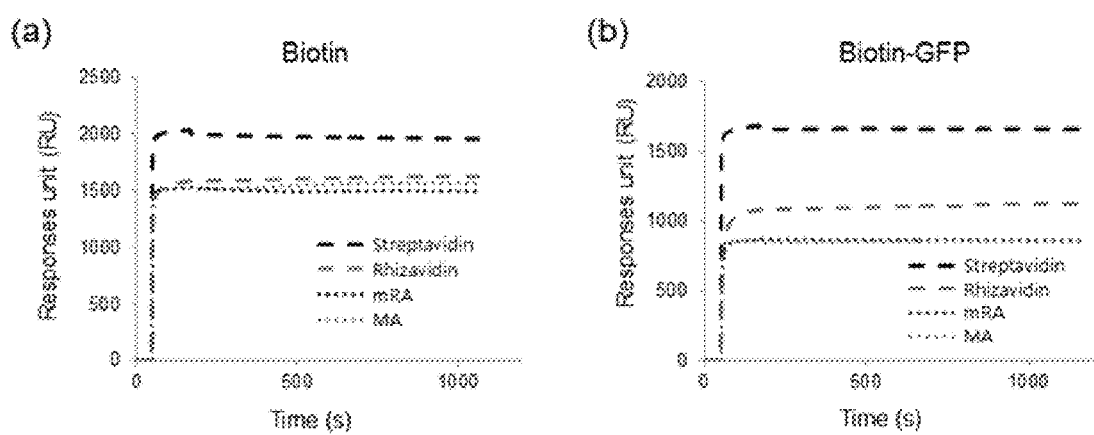

FIG. 13 illustrates surface plasmon resonance (SPR) results of binding stability of avidin proteins to surface-bound (a) biotin and (b) biotin-GFP.

Figure 14:
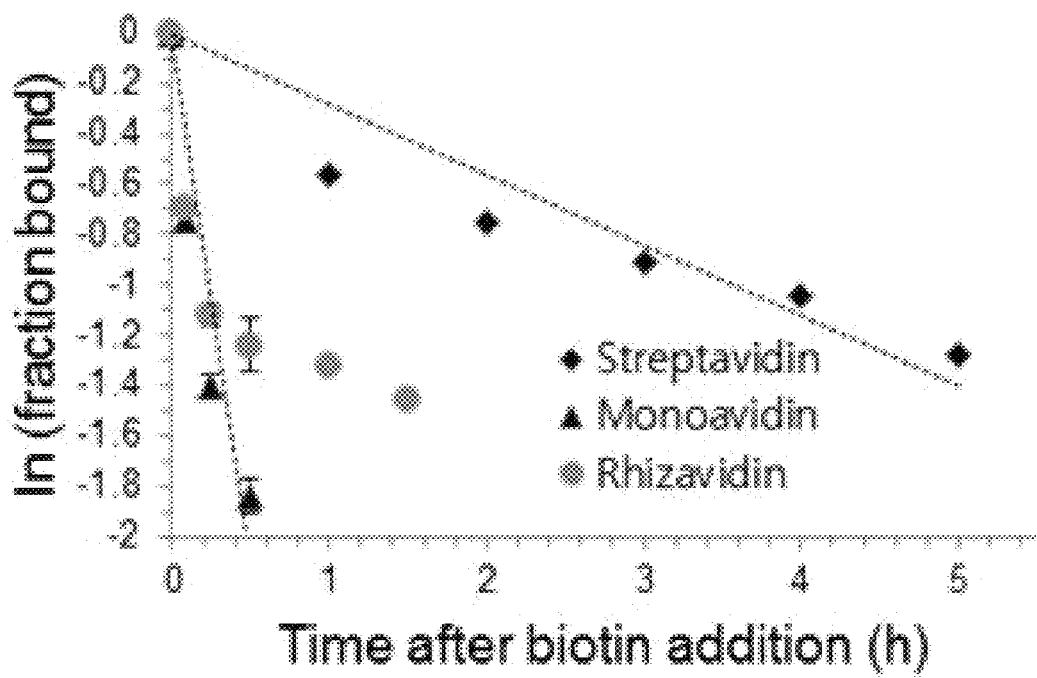

FIG. 14 illustrates dissociation rates of streptavidin (STA), monodin (MA), and rhizavidin (RA) from free [$^3$H]biotin. Avidin proteins were reacted with [$^3$H]biotin, and excess biotin was added to the mixtures. For free biotin, rhizavidin showed non-linear dissociation with $t_{1/2}$ 300 s, and the off-rate of monodin ($1.2\pm0.3\times10^{-5}$ s$^{-1}$) was considerably faster than that of streptavidin ($7.7\pm0.6\times10^{-5}$ s$^{-1}$).

Figure 15:
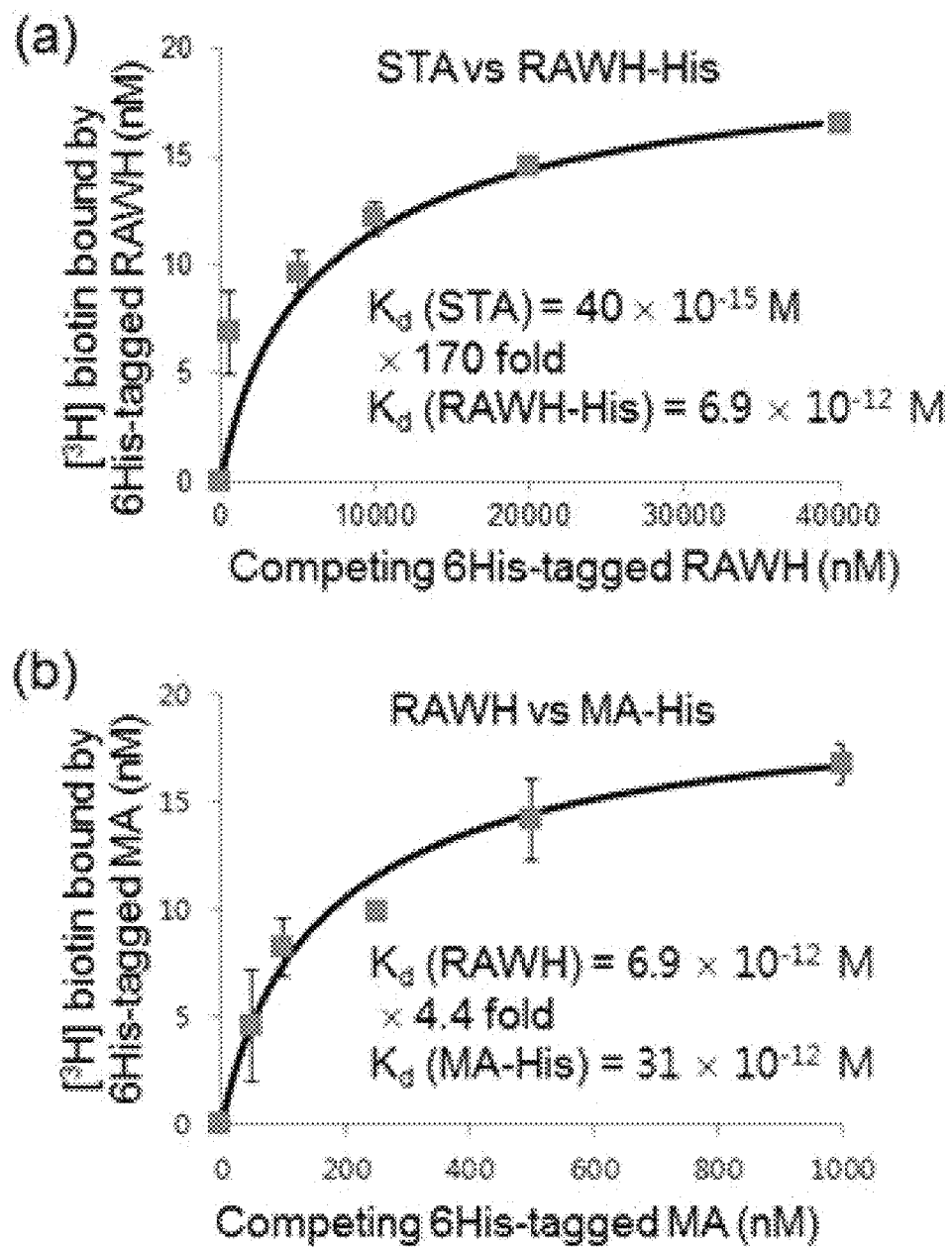

FIG. 15 illustrates relative binding affinities ($K_d$) of a rhizavidin variant (RAWH) and monodin (MA) to free [$^3$H]biotin. (a) The relative binding affinity of RAWH-His was first estimated by analyzing competition binding for [$^3$H]biotin against streptavidin (STA). (b) shows measurement results of $K_d$ of MA-His by analyzing competitive binding with RAWH. Increasing concentrations of RAWH-His (or MA-His) was incubated with 20 nM [$^3$H]biotin and 50 nM streptavidin (or RAWH). After 20 h, RAWH-His (or MA-His) was removed using Ni-NTA agarose, and the amount of [$^3$H]biotin remaining bound to streptavidin (or RAWH) in the supernatant was measured. The relative binding affinity of RAWH-His (6.9 pM) for [$^3$H]biotin was 170-fold weaker than that of streptavidin (40 fM). In addition, the relative binding affinity of monodin (31 pM) for [$^3$H]biotin was 4.4-fold weaker than that of RAWH.

Figure 16:
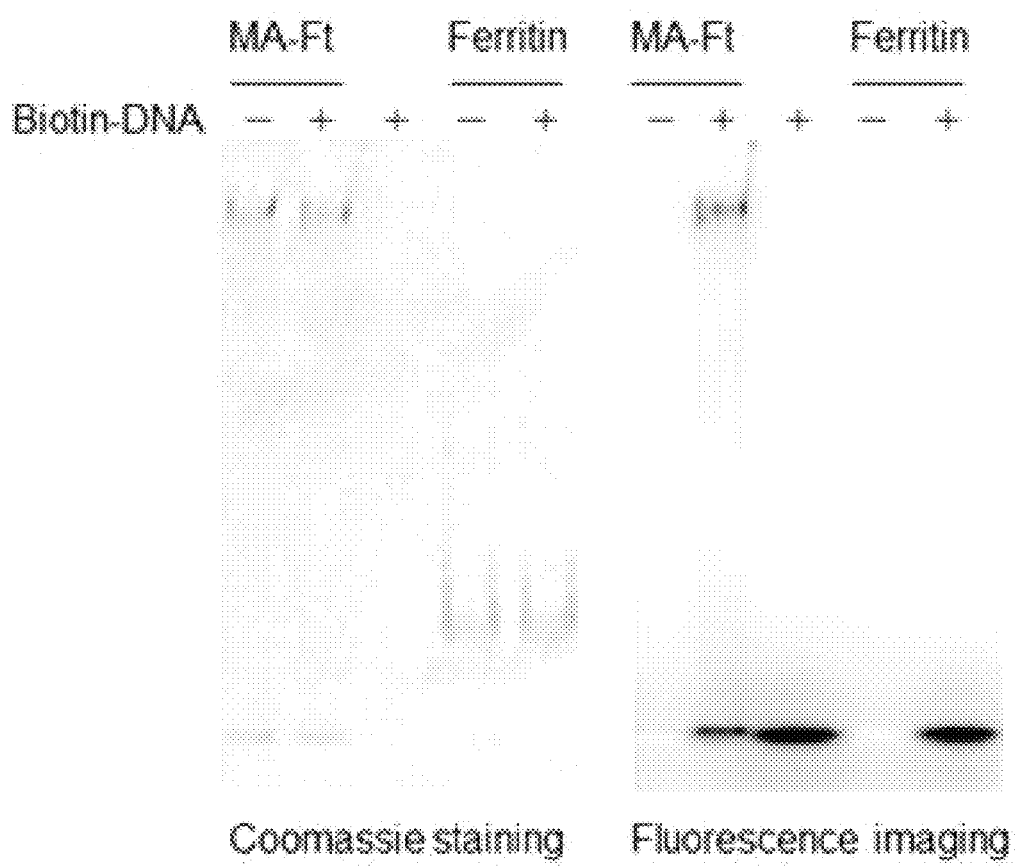

FIG. 16 illustrates native gel analysis of MA-Ft.

Figure 17:
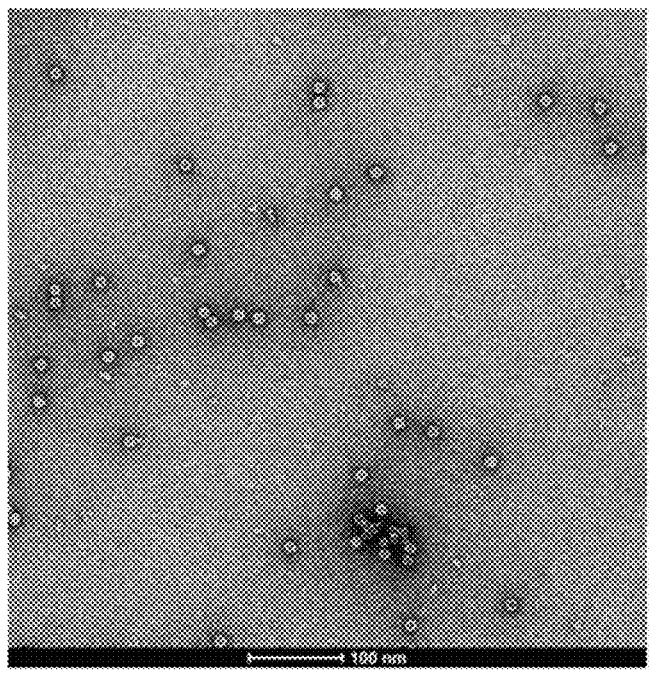
Figure 17:
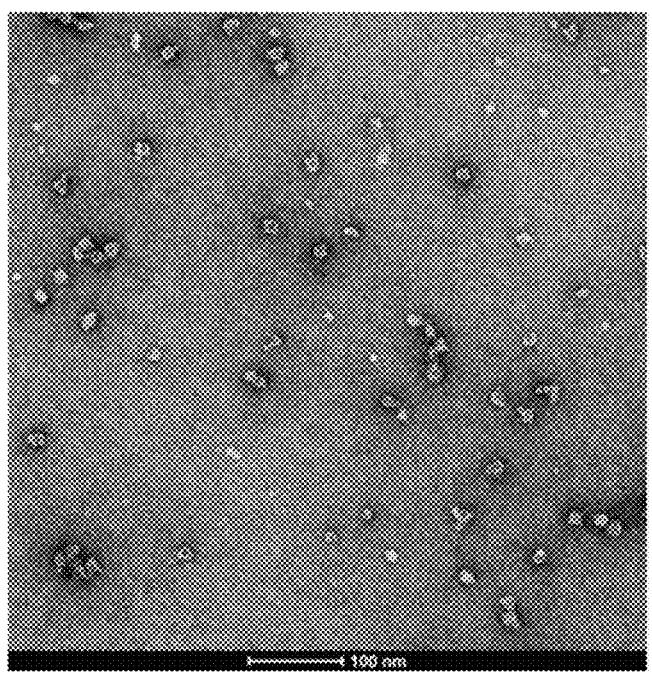

FIG. 17 illustrates TEM images of ferritin and monodin-fused ferritin (MA-Ft). Scale bars: 100 nm.

Figure 18:
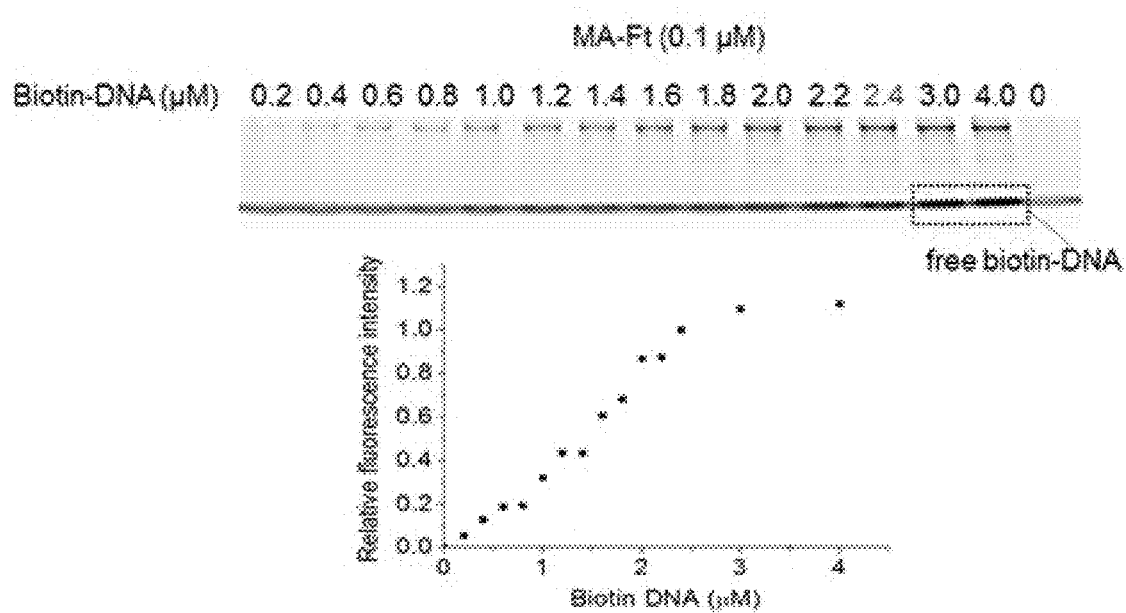

FIG. 18 illustrates binding titration of MA-Ft with a biotinylated DNA probe. 0.1 µM of MA-Ft was titrated with varying concentrations of biotin-DNA (0-4 µM). The fluorescent intensity of the MA-Ft/biotin-DNA complex was saturated between 2.4 µM and 3.0 µM of biotin-DNA (MA-Ft/biotin-DNA molar ratios 1:24-1:30), supporting 24 biotin binding sites of MA-Ft. Free biotin-DNA migrated similar to the loading dye that also shows a weak fluorescence signal in a native gel. Clear levels of free biotin-DNA were observed only with over 2.4 µM of biotin-DNA.

Figure 19:
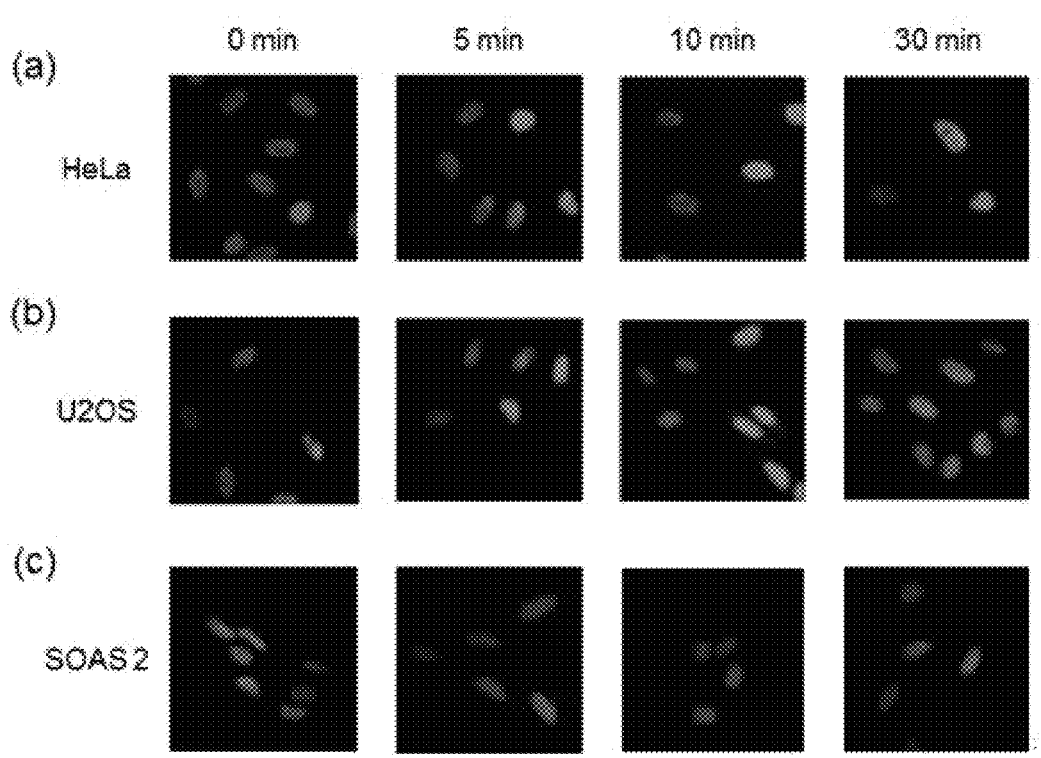

FIG. 19 illustrates non-specific interactions of dye-labeled MA-Ft on non-biotinylated (a) HeLa, (b) U2OS or (c) SOAS2 cells.

Figure 20:
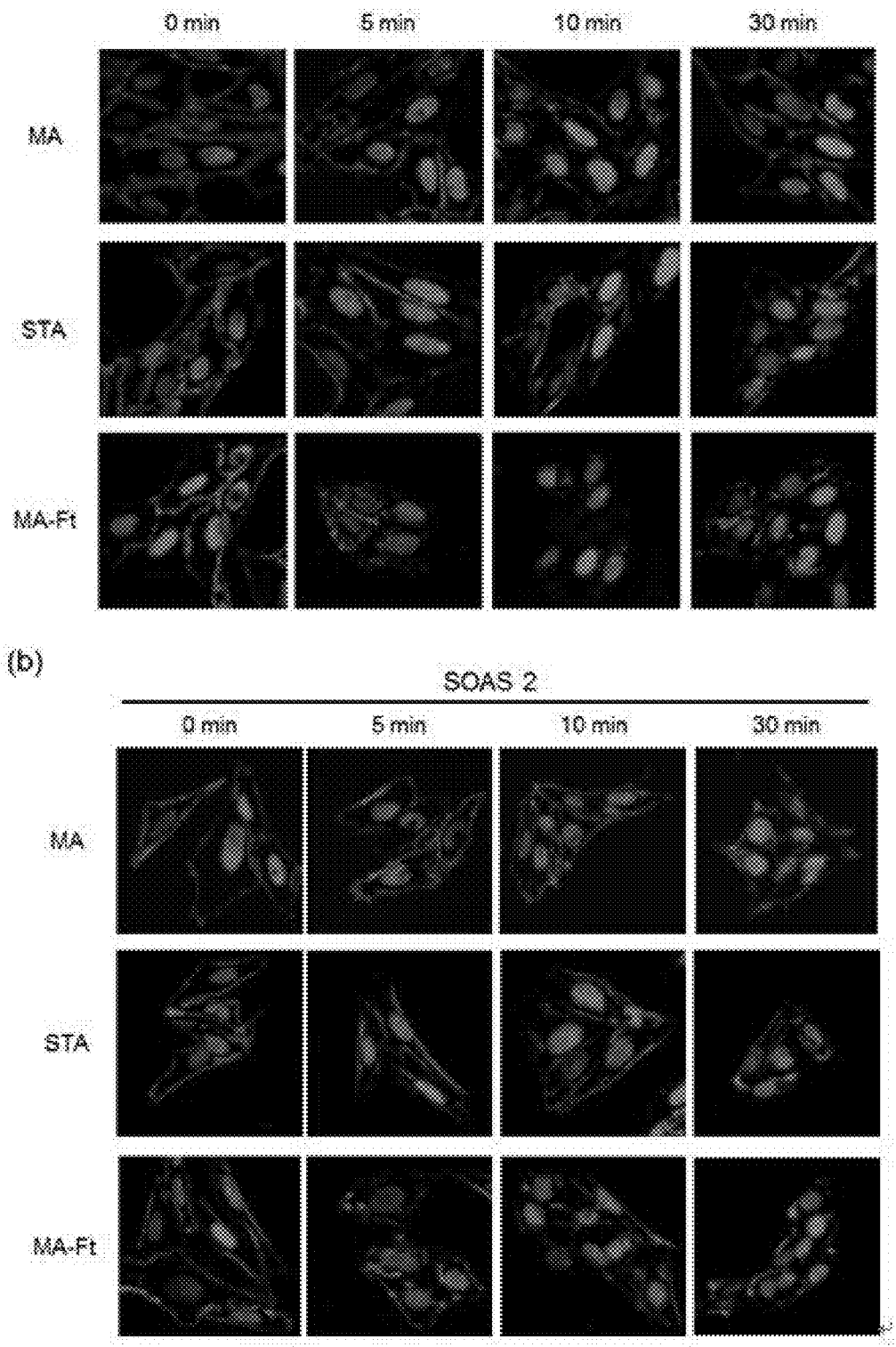

FIG. 20 illustrates artificial clustering surface proteins on (a) U2OS, (b) SOAS2 by mono-(MA), tetra-(STA), and 24-meric (MA-Ft) avidin proteins.

Figure 21:
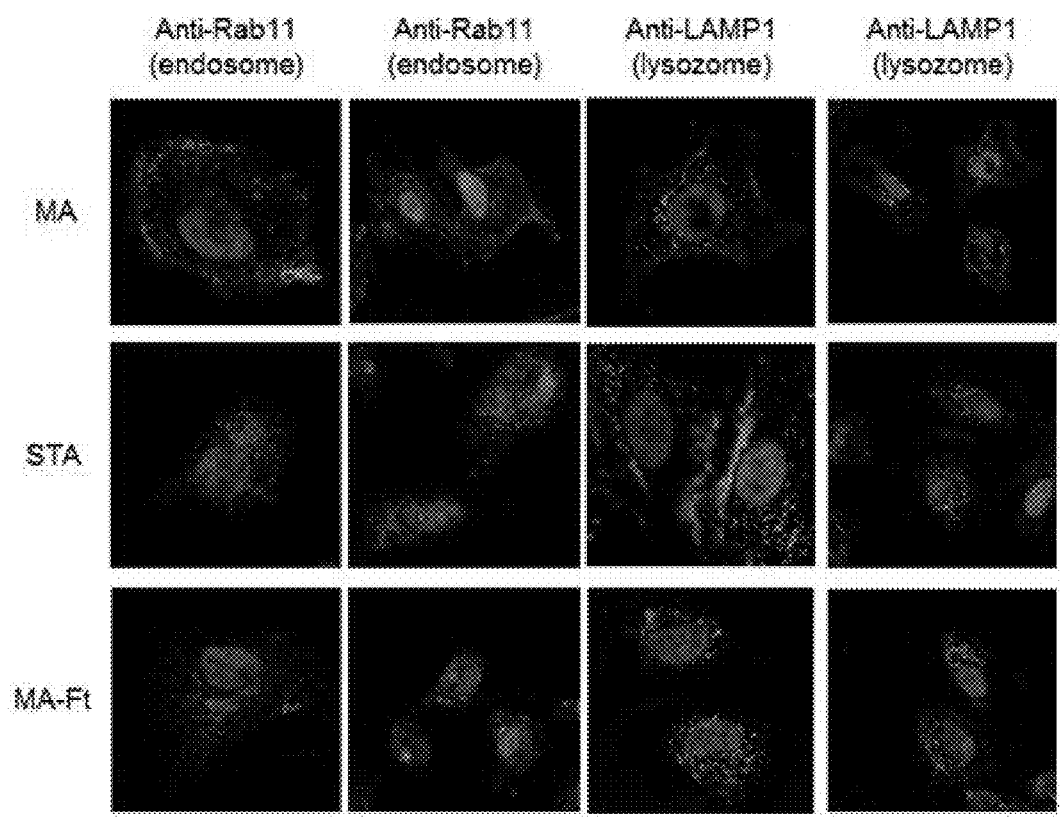

FIG. 21 illustrates localization of internalized proteins by artificial clustering with avidin proteins. Membrane proteins of HeLa cells were randomly biotinylated with Sulfo-NHS-LC-Biotin, and treated with Cy5-conjugated avidin proteins (red). After avidin binding at 4° C. for 20 min, HeLa cells were incubated at 37° C. for 30 min for protein internalization. Cells were then fixed, permeabilized, and then incubated with an anti-Rab11 or anti-LAMP1 antibody for endosomal or lysosomal labeling, respectively. Cells were incubated with a fluorescent secondary antibody (goat anti-rabbit 555, green), and images were acquired with a confocal microscopy.

DETAILED DESCRIPTION

Hereinafter, the present invention will be described in detail with reference to examples. These examples are only for illustrating the present invention more specifically, and it will be apparent to those skilled in the art that the scope of the present invention is not limited by these examples.

EXAMPLES

1. Materials and Methods

Materials

The genomic DNA of Rhizobium etli was purchased from ATCC (51251). All synthetic DNA oligonucleotides were purchased from Bioneer. pfu polymerase (Thermos Scientific) was used for standard polymerase chain reaction (PCT). PCR products and cleaved products by restriction enzymes were purified using DNA purification kit (Biorogen Co.). The restriction enzymes were purchased from Thermo Scientific. Site-directed mutagenesis was performed using QuikChange (Stratagene). Streptavidin was purchased from Abcam. Biotin (Pierce) was dissolved in 100 mM DMSO. Neutravidin (Pierce) was dissolved to 1 mg/ml in PBS. Biotin-AP (SEQ ID NO: 4) was synthesized by Peptron.

Plasmid Construction

The full-length gene of rhizavidin (Gene bank accession number U800928, 34860-35400) was amplified from the genomic DNA of Rhizobium etli. Rhizavidin ($1^{st}$ to $178^{th}$ amino acid residues) was truncated to core rhizavidin ($44^{th}$ to $171^{st}$ amino acid residues, SEQ ID NO: 1), which allowed higher-level protein expression in Escherichia coli (E. coli). Mutants were introduced into the coding sequence of the core rhizavidin using oligonucleotide-directed in vitro mutagenesis. All coding sequences were cloned into the pET21a expression vector (Novagen). To construct biotinylated proteins (biotin-GFP and biotin-protein G), the biotinylation peptide sequence (SEQ ID NO: 4) was added to the N-termini of protein G and negative charged GFP [1]. The genes for these proteins were cloned into the pProExHTa (Invitrogen) expression vector. To construct maltose-binding protein (MBP) fused monomeric and dimeric rhizavidin, the genes of MBP and avidin (RA, mRA, or MA) were amplified using PCR. The PCR products of the MBP were cleaved with restriction enzymes EcoRI/BamHI, and avidin PCR products (RA, mRNA, or MA) were cleaved with restriction enzymes BamHI/XhoI. The MBP and avidin (RA, mRNA, or MA) fragments were ligated to pET21a vector previously cleaved with restriction enzymes ExoRI/XhoI. The human FTH1 (heavy chain ferritin) gene was amplified by PCR from HeLa cDNA. The PCR products of FTH1 were cleaved with BamHI and XhoI, and cloned into pET21a vector. To bind monodin to the N-termini of the human FTH1 via the linker of protein G (MA-Ft), the genes of monodin and protein G were amplified using PCR, and cleaved with restriction enzymes NdeI/EcoRI and EcoRI/BamHI, respectively. DNA fragments were ligated to pET21a/FtH1 vector previously cleaved with NdeI and BamHI.

Protein Preparation

All avidin proteins were expressed in E. coli BL21 (DE3) cells. The transformed cells were grown at 37° C. until $OD_{600}=0.9$, and proteins expressions were induced using IPTG, followed by additional incubation at 37° C. for 4 h. The expression-induced cells were suspended in Buffer A containing 1% Triton X-100 in 1×PBS. After sonication-based breakage, inclusion bodies were isolated from these cell lysates. The inclusion body pellets were washed three times with Buffer A and then dissolved in 6 M guanidinium hydrochloride (GuHCl) with pH 1.5. Proteins in GuHCl were refolded by rapid dilution into PBS at 4° C., and the obtained solutions were stirred overnight. Ni-NTA resin (Qiagen), equilibrated in 250 mM NaCl, 50 mM Tris pH 8.0, and 10 mM imidazole, was added to the refolding solutions, which were further incubated for 4 h at 4° C. The resin was added to a poly-prep column (Bio-Rad), washed with NiNTA washing buffer (300 mM NaCl, 50 mM Tris pH 8.0, 30 mM imidazole), and then eluted with Ni-NTA elution buffer (300 mM NaCl, 50 mM Tris pH 8.0, 200 mM imidazole). Purified proteins were dialyzed three times against PBS, and concentrations were determined after dialysis from $OD_{280}$ using ε280 [2].

Biotin-GFP (SEQ ID NO: 5) and biotin-protein G (SEQ ID NO: 6) were expressed in AVB101 (Avidity), an *E. coli* B strain (hsdR, lon11, SulA1) containing pACYC184 plasmid, which produces biotin ligase BirA upon IPTG induction. Transformed AVB101 cells were grown in the presence of 50 μM biotin, and protein expression was induced by adding IPTG at the final concentration of 1 mM. After sonication-based breakage of expression-induced cells, clarified cell lysates were purified using a Ni-NTA column. Purified proteins were dialyzed against PBS, and stored at −20° C. before use.

MBP fused avidin proteins (SEQ ID NOS: 7-9) were expressed in *E. coli* BL21 (DE3) cells. The transformed cells were grown at 37° C. until $OD_{600}$=0.6, and then protein expressions were induced by 1 mM IPTG, followed by additional incubation at 25° C. for 16 h. The expression-induced cells were suspended in guanidinium lysis buffer (6 M GuHCl, 250 mM NaCl, 50 mM Tris pH 8.0, 10 mM imidazole). After sonication, clarified cell lysates were purified by Ni-NTA columns under denatured conditions. Purified proteins were refolded by rapid dilution into PBS at 4° C., and the obtained solutions were stirred overnight. Ni-NTA resin (Qiagen), equilibrated in 250 mM NaCl, 50 mM Tris pH 8.0, 10 mM imidazole, was added to the refolding solutions, which were further incubated at 4° C. for 4 h. The resin was added to a poly-prep column (Bio-Rad), washed with Ni-NTA washing buffer, and then eluted with Ni-NTA elution buffer. Purified proteins were dialyzed against PBS, and further purified by an amylose column. The final eluates were dialyzed against PBS.

MA-Ft (SEQ ID NO: 10) was expressed in *E. coli* BL21 (DE3) cells. The transformed cells were grown at 37° C. until $OD_{600}$=0.8, and protein expressions were induced by 1 mM IPTG, followed by additional incubation at 37° C. for 4 h. The expression-induced cells were resuspended in Buffer A. After sonication, inclusion bodies were recovered from these cell lysates by centrifugation at 12,000 rpm (4° C., 15 min), washed three times with Buffer A, and then solubilized by incubating in Buffer B containing 8 M urea, 250 mM NaCl, 50 mM Tris pH 8.0 at 4° C. for overnight. Denatured proteins were purified by the Ni-NTA column under denatured conditions. The purified proteins were mixed with an equal volume of Buffer B additionally containing 20 mM DTT to disrupt disulfide bonds, followed by further incubation at room temperature for 4 h. The purified and denatured proteins were refolded by sequentially dialyzing at 4° C. against 4, 3, 2, and 0 M urea in Buffer C (50 mM Tris pH 8.0, 50 mM NaCl, 10% glycerol, 0.1% polyethylene glycol (PEG), 0.2 mM glutathione (reduced), 0.1 mM glutathione (oxidized)) and Buffer D (50 mM Tris pH 8.0, 50 mM NaCl, 10% glycerol).

Avidin proteins were labeled with a 10-fold molar excess of NHS-Cy5 (Invitrogen, stock dissolved to 5 mg/mL in dry dimethylformamide). Following 4 h reaction at 25° C., free dyes were removed by a desalting PD-10 column. Fractions containing labeled proteins were pooled, and free dyes were further removed by three rounds of dialysis in PBS. For gel filtration analysis, protein samples were loaded onto a 10×300 mm superdex 200-size exclusion column, which had been pre-equilibrated with 50 mM Tris pH 7.0, 150 mM NaCl, and eluted with the same buffer at a rate of 0.5 mL/min.

Gel-Based Off-Rate Measurement Against Biotin Conjugates (Biotin-GFP, Biotin-DNA-Fluorescein, Biotin-Protein G-atto532 and Biotin-AP-Fluorescein).

Avidin proteins (1 μM) in 10 μL PBS were mixed with biotin conjugates (0.7 μM biotin-GFP, 0.7 μM biotin-protein G-atto532, 0.7 μM biotin-AP-fluorescein (Peptron), and 0.1 μM biotin-DNA-fluorescein) in 10 μL PBS, and the mixtures were incubated for 30 min at room temperature. Excess biotin (2 mM in 10 μL PBS) was then added to initiate dissociation by blocking biotin non-binding) sites (free biotin binding sites) of avidin proteins. After incubation at the indicated temperature (23° C., 37° C., or 45° C.) for varying time points (between 0 to 10 h), protein-conjugate mixtures were loaded onto a 15% native polyacrylamide gel. Native-PAGE was performed at 300 V for 15-25 min using a standard 2-D Electrophoresis System (Hoefer) with cooling water flowing through the plates to prevent dissociation of avidin proteins from biotin conjugates during electrophoresis. Fluorescence images of native gels were obtained using a laser gel-scanner (Typhoon, GE Healthcare), and the degrees of biotin conjugates dissociated from avidin proteins were measured by platting image quant 5.2. Data as ln(fraction bound) versus time and fitting the data to a straight line by linear regression. Dissociation rates were deduced from the slope of the line and the following equation:

$$\ln(\text{fraction bound}) = -k_{off}(t)$$

where fraction bound=(total biotin-conjugate−free biotin-conjugate at time point)/(total biotin conjugate−free biotin-conjugate before excess biotin addition).

[$^3$H]Biotin Off-Rate Assay

To determine off-rates of free biotin from MA or wild type streptavidin, 50 nM [$^3$H]biotin (Amersham) was pre-incubated with 1 μM MA or wild type streptavidin at 25° C. for 30 min. Dissociation was then initiated by addition of cold biotin at a final concentration of 500 μM. At time-points taken over 5 h at 37° C., 150 μL of aliquots were removed, and added to 600 μL of 0.2 M $ZnSO_4$ (chilled with ice), followed by addition of 600 μL of 0.2 M NaOH. The protein precipitate was pelleted by centrifugation at 13,500 rpm for 5 min, and [$^3$H]biotin in the supernatant was measured by a liquid scintillation counter (Beckman Coulter). Dissociation rates were deduced as discussed above.

$K_d$ Measurements

The relative binding affinities of rhizavidin (RA) and monodin (MA) to free biotin were estimated by analyzing competition with streptavidin ($K_d$~40 fM) for [$^3$H]biotin at 37° C. A rhizavidin variant (RAWH) with an enhanced biotin binding affinity by introducing E115W and S23H mutations was prepared. Wild type streptavidin (50 nM biotin binding subunit) was mixed with 20 nM [$^3$H]biotin and 0-40 μM competing RAWH-His6 in PBS. To determine relative $K_d$ of MA, RAWH (50 nM biotin binding subunit) without a His tag was mixed with 20 nM [$^3$H]biotin and 0-1 μM competing MA-His6 in PBS. Mixtures were incubated at 37° C. for 20 h to reach equilibration. To separate the His6-tagged RAWH (or MA-His6) from wild type streptavidin (or from RAWH), an equal volume of 50% slurry of Ni-NTA beads (Qiagen) in PBS with 15 mM imidazole was added. After 1 h incubation at room temperature, the beads were cleared by centrifugation at 13,000 rpm for 1 min. Aliquots were taken from the supernatant containing the biotin-bound wild type streptavidin (or RAWH), and combined with an equal volume of 10% SDS in water. Samples were heated to 95° C. for 30 min, and then counted in a liquid scintillation counter. The $K_d$ ratios between competing avidin proteins were calculated with Matlab (Mathworks) using the foregoing formula (Qureshi, M. H. & Wong, S. L. Protein Expr. Purif. 25, 409-415 (2002)).

Surface Plasmon Resonance (SPR) Analysis

SPR tests were performed in a Biacore 3000 instrument using dextran CM5 gold chips (GE Healthcare) and a PBS buffer as a running solution. To introduce biotin on the chip surface, diamine (sigma) was first immobilized, and subsequently reacted with NHS-biotin on flow cells. Alternatively, biotin-GFP was directly immobilized on CM5 chips via a standard EDC/NHS conjugation procedure as described in the manufacturer's protocol. Avidin proteins (5 µM) were flown over immobilized biotin or biotin-GFP at a rate of 30 µL/min.

Transmission Electron Microscopy (TEM)

Various avidin-fusion proteins were adsorbed to carbon grids, and negatively stained with 0.75% uranyl formate. Electron micrographs were acquired with a 4 K×4 K Eagle HS CCD camera (FEI) on a Tecnai T120 microscope (FEI) at 120 kV. Images were taken at a magnification of ×67,000 and defocus settings ranging from −1.4 to −1 µm.

Measurement of Diffusion Constants Via Fluorescence Single-Molecule Tracking

For the study of diffusion of a single lipid labeled by MA, supported bilayer membranes were prepared on cover glasses via vesicle fusion [5]. The present inventors prepared a lipid mixture of 1 mol % biotinylated 1,2-di(9Z-octadecenoyl)-sn-glycero-3-phosphocholine (DOPC, Avanti Polar Lipids) and 99 mol % 1,2-Dioleoyl-sn-glycero-3-phosphocholine (DOPC, Avanti Polar Lipids) for dye-conjugated MA labeling. In the control experiment, a trace amount (~$10^{-6}$ mol %) of dye-labeled lipids, atto532-1,2-dioleoyl-sn-glycer-3-phosphoethanolamine (atto532-DOPE, ATTO-TEC-GmbH), was added into the DOPC lipids. The detailed procedures of preparing supported lipid bilayers can be well known (Laitinen, O. H. et al. J. Biol. Chem. 278, 4010-4014 (2003)). Briefly, the lipid mixture was dried in a glass vial with a stream of nitrogen, and put in a desiccator overnight to remove the organic solvent completely. The dried lipids were hydrated in HEPES buffer (150 mM NaCl and 10 mM HEPES) for 1 h. The hydrated lipid solution was treated with ultrasound (Q700, Qsonica) for 20 min, during which the lipid vesicles were formed. The lipid solution was centrifuged at 16,000 g for 20 min at 4° C. to remove large lipid clusters. The vesicles in the supernatant were collected for preparation of supported lipid bilayers. Cover glasses were cleaned thoroughly by 2% Hellmanex, followed by treatment with 1 M KOH for 15 min and extensive rinsing with deionized water. The cover glass was then treated with oxygen-plasma for 5 min right before adding the lipid vesicle solution. Lipid bilayer membranes were formed on the cover glass spontaneously within 10 min. Excess vesicles were removed by buffer exchange.

Individual biotin-cap-DOPE (labeled with dye-conjugated MA) and atto532-DOPE were directly observed under a home-built inverted epi-fluorescence microscope. The wide-field excitation of ~1 kW/cm$_2$ on the sample was created by focusing a 532 nm laser beam at the back focal point of a microscope objective (100×, NA 1.4). The epi-fluorescence image was monitored by an EMCCD camera. Diffusive motion of single molecules on the membrane was recorded in fluorescence at 100 frames per second. From the recorded video, positions of single molecules were determined in every frame with a localization precision of ~35 nm. Diffusion trajectories were obtained by connecting the corresponding localizations in the consecutive frames. Only diffusion trajectories that are longer than 50 steps were considered for further analysis. Time-averaged mean squared displacement (MSD) was then calculated from each diffusion trajectory. The diffusion constant of each trajectory was found from the first two data points of the MSD.

Cell Culture and Imaging

Cells (HeLa, U2OS, and SOAS2) at 70-80% confluency were washed three times with cold PBS-CM (PBS with 1 mM CaCl2, 0.1 mM MgCl2) and were incubated with 0.25 mM Sulfo-NHS-LC Biotin in PBS-CM for 30 min on ice. Following biotinylation, the cells were washed twice with cold PBS-CM, treated with 100 mM glycine in PBS-CM for blocking, and washed again twice with cold PBS. The biotinylated cells were treated with 1.5 µM Cy5-labeled avidin proteins in DMEM, which was pre-treated to remove biotin, on ice for 20 min. Unbound avidin proteins were removed, and media was replaced with pre-warmed DMEM (37° C.). Cells were incubated for 5, 10, or 30 m at 37° C. Cells were washed, and fixed with 4% formaldehyde in PBS for confocal imaging (ZEISS, LSM510 META). To visualize endosome or lysozome-specific proteins, cells were fixed, permeabilized, and incubated with a primary antibody: anti-Rab11 (a GTPase of recycling endosome, Abcham) or anti-LAM P1 (Lysosomal-associated membrane protein 1, Abcham). Afterward, cells were incubated with a fluorescent secondary antibody (goat anti-rabbit 555, Abcham), and images were acquired with a confocal microscopy (ZEISS, LSM510 META).

2. Results

Figure 1:
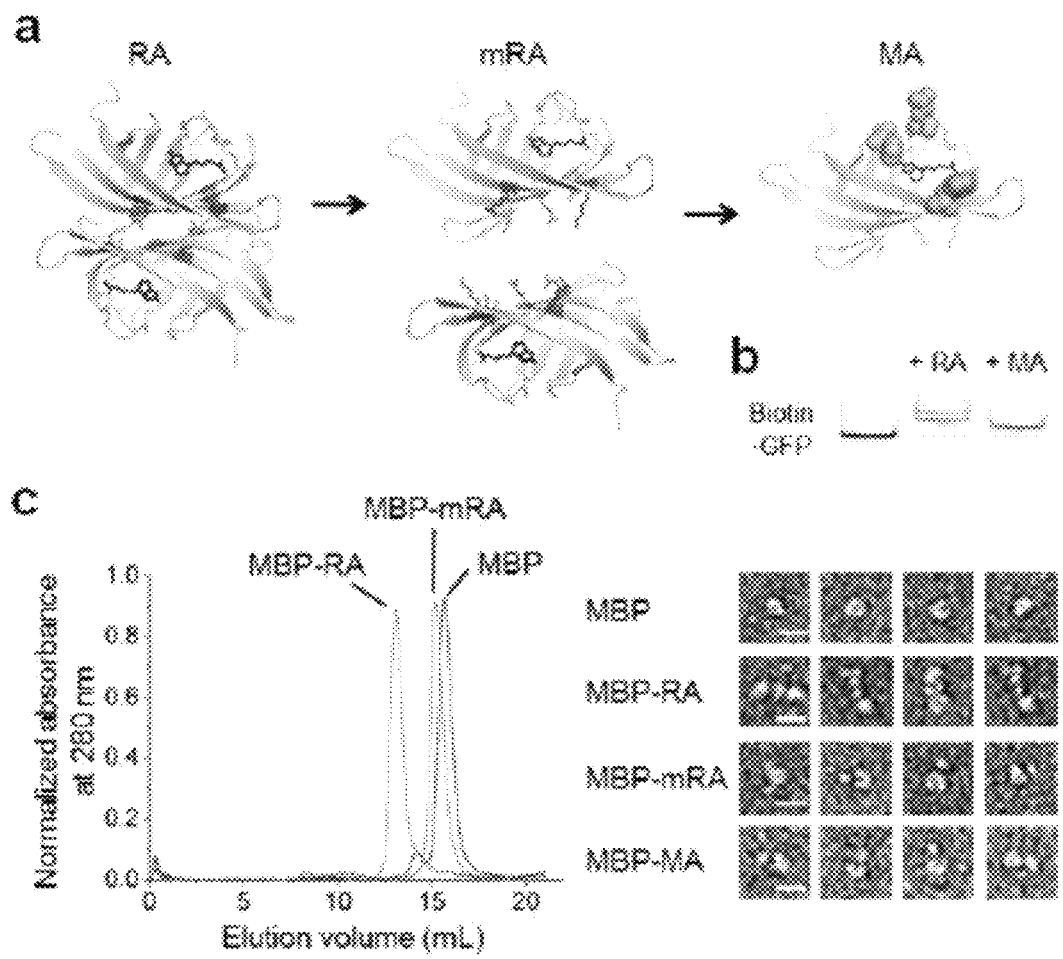
FIG. 1 illustrates the production of a monomeric avidin-like protein. (a) Schematic diagram for engineering monomeric rhizavidin (mRA) and monodin (MA) from dimeric rhizavidin (RA). (b) Native-gel analysis of complex formation between biotin-GFP and dimeric RA or monomeric MA. (c) Size exclusion chromatography (left) and representative TEM images (right) of MBP and MBP-fused avidin proteins. Scale bars: 5 nm
Figure 4:
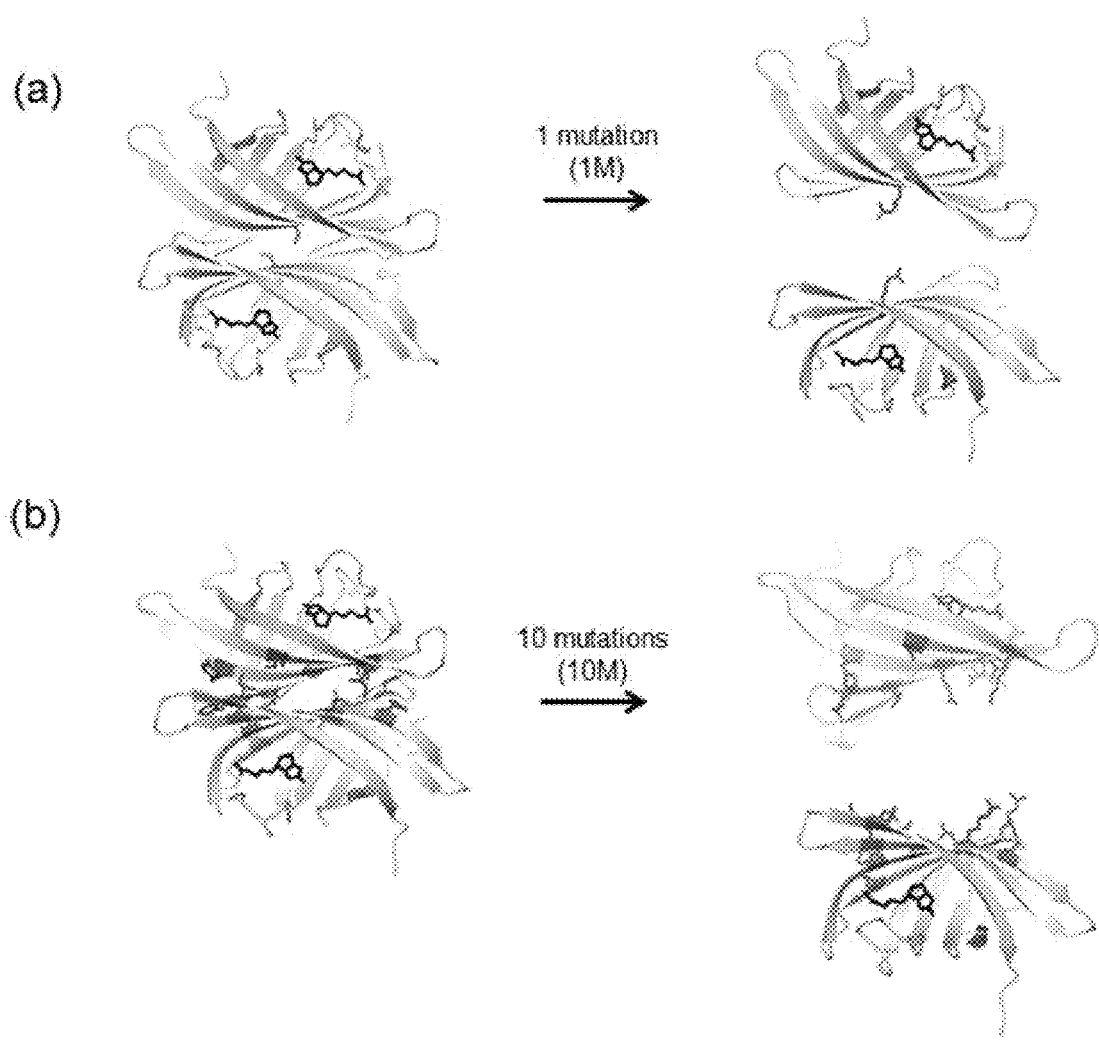
FIG. 4 illustrates the construction of monomeric avidin-like proteins. Schematic diagram for engineering monomeric rhizavidin with (a) one mutation (1M: S69R) or (b) ten mutations (10M: A67K, G71K, S101R, A105K, A82N, G84Q, F345, F65R, Y88H, I114D) from dimeric rhizavidin (RA). Biotin (black) and mutated residues (red and blue) are indicated.
Figure 5:
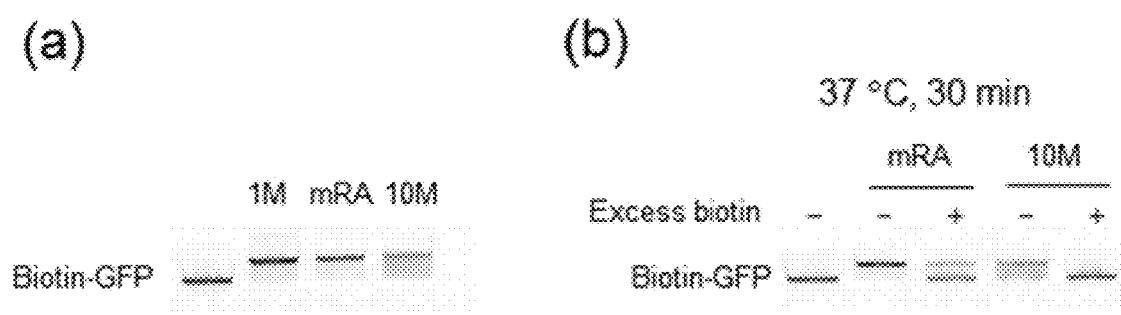
FIG. 5 illustrates biotin binding of monomeric avidin-like proteins. (a) Native-gel analysis of biotin binding characteristics of monomerized rhizavidin proteins (1M, mRA, 10M). The proteins were reacted with a biotinylated green fluorescent protein (biotin-GFP), and protein complexes were analyzed by 15% native-PAGE. (b) Binding stability of monomerized rhizavidin variants (mRA, 10M) for biotin-GFP in excessive biotin conditions. mRA and 10 M were reacted with biotin-GFP. After incubation with excess biotin at 37° C. for 30 min, the mixtures were analyzed using 15% native-PGA. While small amount of biotin-GFP was dissociated from mRA, most biotin-GFP was released from 10 M.

Rhizavidin (RA) from *Rhizobium etli* is the first natural dimer in the avidin protein family with a high binding affinity for biotin (Helppolainen, S. H. et al. Biochem. J. 405, 397-405 (2007)). Interestingly, the biotin-binding pocket of rhizavidin consists of residues from a single monomer subunit, without tryptophan that is essential for tetrameric avidin homologs (Meir, A. et al. J. Mol. Biol. 386, 379-390 (2009)). Dimeric rhizavidin, however, contains a characteristic disulfide bond in the biotin binding site, which restrains the protein and leads to a rigid and preformed binding pocket for tight biotin binding. Therefore, the present inventors envisioned that a monomeric avidin protein with a high binding affinity for biotin could be derived from rhizavidin by monomerizing the dimer while minimally altering its natural structure, especially the rigid binding pocket. To monomerize rhizavidin, the present inventors introduced various numbers (one, six, and ten) of charged and hydrophilic amino acids, which have long side chains, at the dimeric interface (FIG. 1(a) and FIG. 4). The biotin binding properties of the rhizavidin variants were investigated by a gel mobility shift assay with a biotinylated green fluorescent protein (FIG. 1(b) and FIG. 5). Divalent wild type rhizavidin formed two separated complexes, whereas all the rhizavidin mutants formed a single complex with biotin-GFP, thus indicating successful monomerization of the protein. Of the monomerized proteins, the monomeric rhizavidin with six interfacial mutations, which are termed mRA, contains optimal modifications to stabilize the exposed dimeric interfaces as well as to maintain the rigid structure of rhizavidin for tight biotin binding (FIG. 5).

The relative dissociation of mRA from biotin-GFP by excess free biotin was still, however, much faster than that of dimeric rhizavidin (FIG. 6), likely due to the inevitable loss of the overall protein rigidity by monomerization. Two amino acids (E115 and S23) near the entrance of the biotin binding site were mutated into various large (often hydrophobic) amino acid residues for biotin shielding (FIG. 1(a), Hyre, D. E. et al. Nat. Struct. Biol. 9, 582-585 (2002)). In addition, a residue Q46 near E115 and S23 was mutated to a charged residue to maintain protein solubility by compensating for the enhanced hydrophobicity. Among many constructed mRA variants, the E115W/S23H/Q46E mutants showed a highly slowed off-rate from biotin-GFP, where dissociation was even similar to that of the original dimeric rhizavidin (FIG. 7). The present inventors termed the optimized monomeric rhizavidin as monodin (MA). The monomeric structures of mRA and MA were further confirmed by size-exclusion chromatography (SEC) and transmission electron microscopy (TEM) (FIG. 1(c)). The relatively large maltose binding protein (MBP, ~44 kDa) was fused to both monomeric and dimeric rhizavidin proteins to improve the differences in the size as well as the shape of these proteins. Monodisperse and size-dependent elution profiles of free MBP and MBP-fused proteins support the highly homogeneous monomeric structure of monomerized rhizavidin proteins (FIG. 1(c) and FIG. 8). A single MBP is linked to monomeric mRA as well as MA, whereas MBP is dimerized by genetic fusion to dimeric rhizavidin (FIG. 1(c), and FIG. 9).

Figure 2:
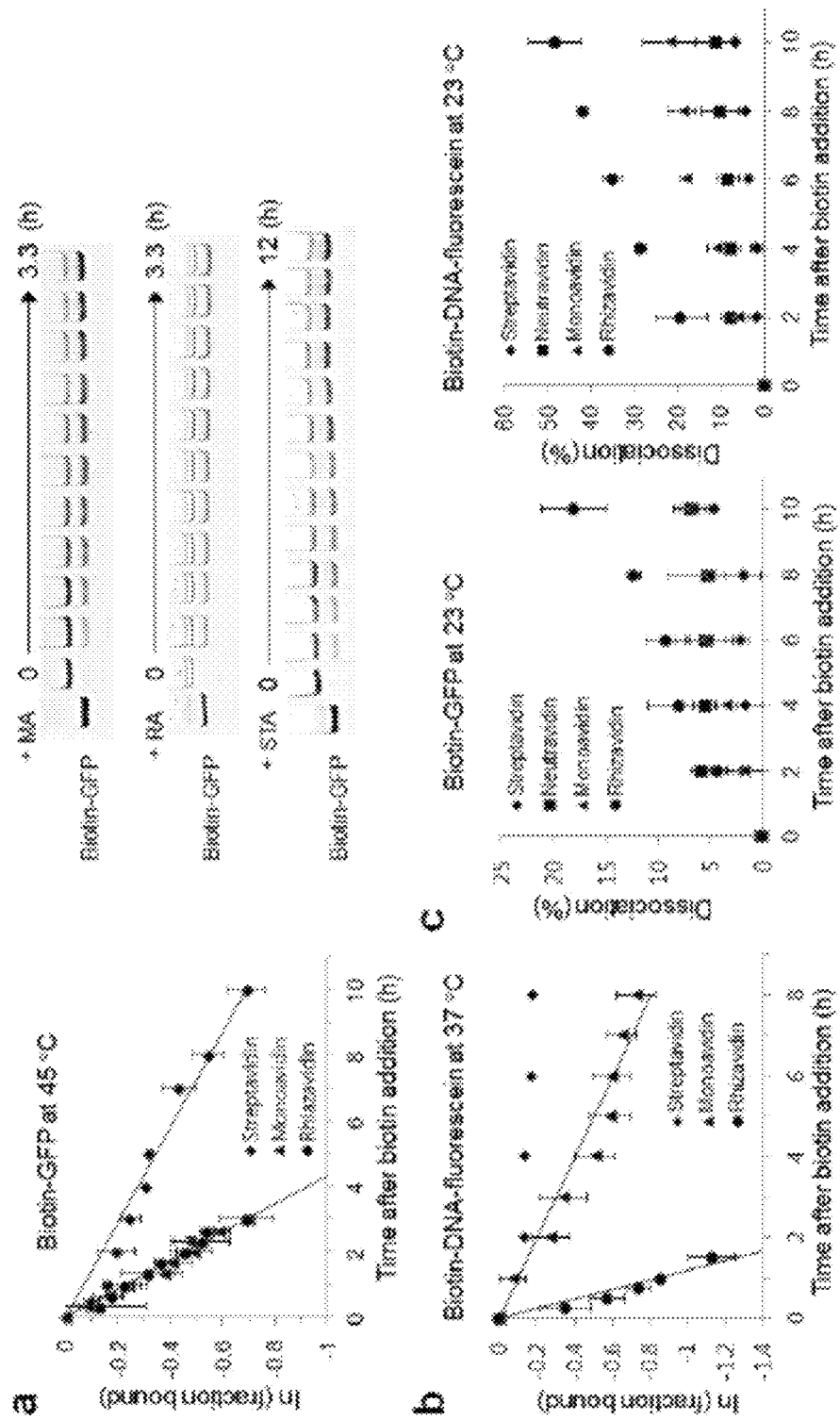
FIG. 2 illustrates dissociation rates of avidin proteins from biotin conjugates. (a) Off-rates from biotin-GFP at 45° C. Biotin-GFP was mixed with streptavidin (STA), rhizavidin (RA), or monodin (MA). After various incubation times with excess biotin at 45° C., the dissociated biotin-GFP was separated and measured on a 15% native-polyacrylamide gel (right). (b) Off-rates from biotin-DNA-fluorescein at 37° C. (c) Dissociation rates of avidin proteins from biotin-GFP (left) and biotin-DNA-fluorescein (right) at 23° C. Error bars: 1 s.d. (n=3).

The stability of MA binding to various biotin conjugates was evaluated by measuring off-rates under excess biotin at diverse temperatures. At 45° C., the dissociation rate constant of MA from biotin-GFP was $6.4\pm0.2\times10^{-5}$ S$^{-1}$, which is nearly equal to that of rhizavidin, and only 3.4-fold faster than that of tetrameric streptavidin (FIG. 2(a) and table 1). At 37° C., the off-rate for MA ($2.3\pm0.1\times10^{-5}$ S$^{-1}$) indicated a dissociation half-life of 8.3 h, which is even slower than that of rhizavidin (3.8 h).

The similar biotin binding stability of MA was also observed against another biotinylated protein as well as a peptide (FIG. 10). The present inventors also conducted tests on the binding of biotinylated DNA to the avidin proteins. Interestingly, the dissociation of wild-type rhizavidin from biotin-DNA ($23\pm0.1\times10^{-5}$ S$^{-1}$) was considerably faster than that of MA ($2.7\pm0.3\times10^{-5}$ S$^{-1}$) at 37° C. (FIG. 2(b) and FIG. 11). In the cases of tetrameric streptavidin and neutravidin, only about 20% of the avidins were dissociated from biotin-DNA, even after incubation at 37° C. for 10 h (table 1). Impressively, at 23° C., monodin also showed only 22% dissociation from biotin-DNA after incubation for 10 h (FIGS. 2(c) and 12). Moreover, MA dissociation from biotin-GFP at 23° C. was similar to those of neutravidin and streptavidin (less than 7% dissociation after 10 h). The above results indicate that MA of the present invention has high stability to bind to various biotin conjugates, such as having the off-rate compared to (or even improved than) the dimeric rhizavidin. Dissociation of MA from surface-bound biotin conjugates was not observed by surface plasmon resonance (SPR) analysis (FIG. 13). Against free biotin, MA showed a faster off-rate ($1.2\pm0.3\times10^{-3}$ s$^{-1}$) with a relative $K_d$ value of $31\pm10$ pM at 37° C., which was estimated by analyzing the competition with streptavidin ($K_d$~40 fM) for [³H]biotin (FIGS. 14 and 15).

TABLE 1

| Biotin-conjugate | Temperature | Protein | Dissociation rate (s$^{-1}$) |
|---|---|---|---|
| Biotin-GFP | 45° C. | Monodin (MA) | $6.4 \pm 0.2 \times 10^{-5}$ |
| Biotin-GFP | 45° C. | Rhizavidin (RA) | $6.0 \pm 0.6 \times 10^{-5}$ |
| Biotin-GFP | 45° C. | Streptavidin (STA) | $1.9 \pm 0.2 \times 10^{-5}$ |
| Biotin-GFP | 45° C. | Neutravidin (NA) | $32 \pm 5.0\%$ for 10 h* |

TABLE 1-continued

| Biotin-conjugate | Temperature | Protein | Dissociation rate (s$^{-1}$) |
|---|---|---|---|
| Biotin-GFP | 37° C. | Monodin (MA) | $2.3 \pm 0.1 \times 10^{-5}$ |
| Biotin-GFP | 37° C. | Rhizavidin (RA) | $5.0 \pm 0.1 \times 10^{-5}$ |
| Biotin-GFP | 37° C. | Streptavidin (STA) | $22 \pm 4.4\%$ for 10 h* |
| Biotin-GFP | 37° C. | Neutravidin (NA) | $16 \pm 3.8\%$ for 10 h* |
| Biotin-GFP | 23° C. | Monodin (MA) | $6.7 \pm 1.1\%$ for 10 h* |
| Biotin-GFP | 23° C. | Rhizavidin (RA) | $18 \pm 3.0\%$ for 10 h* |
| Biotin-GFP | 23° C. | Streptavidin (STA) | $4.7 \pm 0.3\%$ for 10 h* |
| Biotin-GFP | 23° C. | Neutravidin (NA) | $6.8 \pm 1.6\%$ for 10 h* |
| Biotin-protein G | 37° C. | Monodin (MA) | $4.6 \pm 1.5 \times 10^{-5}$ |
| Biotin-protein G | 37° C. | Rhizavidin (RA) | $3.2 \pm 0.8 \times 10^{-5}$ |
| Biotin-AP | 37° C. | Monodin (MA) | $5.1 \pm 0.7 \times 10^{-5}$ |
| Biotin-AP | 37° C. | Rhizavidin (RA) | $4.9 \pm 0.7 \times 10^{-5}$ |
| Biotin-DNA | 37° C. | Monodin (MA) | $2.7 \pm 0.3 \times 10^{-5}$ |
| Biotin-DNA | 37° C. | Rhizavidin (RA) | $23 \pm 0.1 \times 10^{-5}$ |
| Biotin-DNA | 37° C. | Streptavidin (STA) | $17 \pm 1\%$ for 10 h* |
| Biotin-DNA | 37° C. | Neutravidin (NA) | $20 \pm 0.2\%$ for 10 h* |
| Biotin-DNA | 23° C. | Monodin (MA) | $22 \pm 6.0\%$ for 10 h* |
| Biotin-DNA | 23° C. | Rhizavidin (RA) | $48 \pm 6.1\%$ for 10 h* |
| Biotin-DNA | 23° C. | Streptavidin (STA) | $6.8 \pm 1.8\%$ for 10 h* |
| Biotin-DNA | 23° C. | Neutravidin (NA) | $11 \pm 4.4\%$ for 10 h* |

*Off-rates that are slower than $1.0 \times 10^{-1}$ s$^{-1}$ cannot be reliably measured by the present gelbased method. Therefore, percentages of dissociated biotin conjugates were measured after 10 h incubation with excess biotin. Data were obtained from at least three independent experiments.

Figure 3:
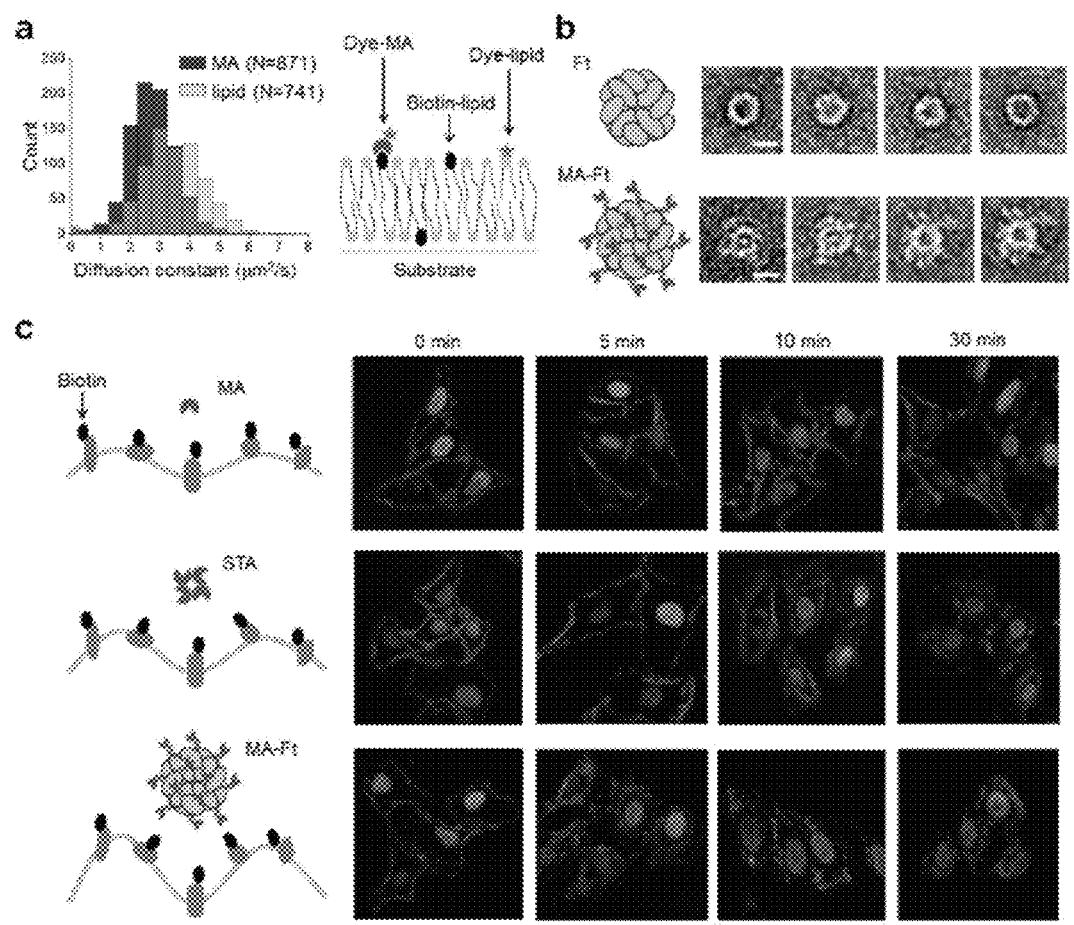
FIG. 3 illustrates Novel mono- and high-valent MA probes. (a) Histograms of diffusion constants of single-dye-labeled lipids and MA-labeled lipids in supported lipid bi-layers. (b) Representative TEM images of 24-meric human ferritin (Ft) and MA-fused ferritin (MA-Ft). Scale bars: 10 nm. (c) Artificial clustering of cell-surface proteins by mono- (MA), tetra- (STA), and 24-meric (MA-Ft) avidin proteins. Cell-surface proteins were randomly biotinylated and treated with Cy5-labeled avidin proteins at 4° C. Cell-surface labeling and subsequent internalization of avidin proteins were monitored at various time points during incubation for 30 min at 37° C.

To investigate the monovalent (and thereby nonperturbing) biotin labeling by MA, the lateral diffusion dynamics of head-group-biotinylated lipids were measured on supported bilayer membranes labeled with dye-conjugated MA (FIG. 3(a)). Diffusion trajectories of single-dye-conjugated MA labeled on the biotinylated lipids were directly observed under a fluorescence microscope (see Video S1). The lipids labeled with dye-conjugated MA showed similar diffusion constants as the lipids labeled with small atto-dye molecules (FIG. 3(a)), which indicates that the labeling of MA is monovalent and does not modify the mobility of single lipids in the bilayer membranes. Biotin-lipid diffusion constants were previously found to be significantly reduced (more than twice) by multivalent labeling with streptavidin-conjugated quantum dots (Farlow, J. et al. Nat. Methods 10, 1203-1205 (2013)).

In addition to monovalent biotin labeling, monomeric MA can be fused with diverse multimeric proteins to create new multivalent avidin probes. Here, the present inventors fused MA to 24-meric human ferritin, which is a cage-like protein with a diameter of ~12 nm (Crichton, R. R. & Declercq, J. P. Biochim. Biophys. Acta 1800, 706-718 (2010)). Monodin-fused ferritin (MA-Ft) may have 24 biotin binding sites displayed symmetrically on the protein cage surface (FIG. 3(b)). Native gel analyses confirmed that the fabricated MA-Ft has a monodisperse protein structure with a high molecular weight as well as MA having biotin binding ability (FIG. 16). In addition, TEM images clearly revealed that MA-Ft was assembled into the cage-like structure and MA proteins were well displayed on the exterior surface of the ferritin cage (FIG. 3(b) and FIG. 17). A binding titration of MA-Ft with a biotinylated DNA probe strongly indicated that all 24 MA subunits of MA-Ft are able to bind the biotin-conjugated ligand (FIG. 18).

Next, the present inventors applied MA and MA-Ft to examine how enhanced cross-linking of cell-surface proteins affects the internalization rates of these proteins in live cells. Asymmetric protein crowding on a lipid bilayer and subsequent membrane bending is one of the proposed mechanisms for the generation of biomembrane curvatures, which is also likely to contribute to membrane internalization (Kirchhausen, T. Nat. Cell Biol. 14, 906-908 (2012); Stachowiak, J. C. et al. Nat. Cell Biol. 14, 944-949 (2012); Derganc, J., Antonny, B. & Copic, A. Trends Biochem. Sci. 38, 576-584 (2013)). However, little is known regarding how cell-surface membranes react to the artificial clustering of membrane-bound proteins. To generate various protein clusters on a live cell surface, membrane proteins were randomly biotinylated using a cell-impermeable agent, and subsequently treated with dye-conjugated avidin proteins from monomeric MA, tetrameric STA, to 24-meric MA-Ft (FIG. 3(c)). Following avidin binding at 4° C., plasma membrane activities were initiated by a temperature change to 37° C. Monodin proteins (and biotin-labeled membrane proteins) on HeLa cells were slowly internalized after 30 min, whereas streptavidin proteins were visibly internalized after only 10 min (FIG. 3(c)). Interestingly, 24-valent MA-Ft was nearly immediately internalized, with the protein signals being full inside the cytosols after incubation for 5 min at 37° C. The fluorescence signals of avidin proteins are biotin-specific, with no signals being detected without biotinylation (FIG. 19). Rapid internalization by MA-Ft clustering was also observed in other cell lines, such as U2OS and SOAS2 cells (FIG. 20). Internalized proteins appeared to remain clustered inside cells during incubation for 30 min without specific targeting to certain organelles (FIG. 21).

Although more studies are needed to elucidate the physical or cellular mechanism of clustered protein internalization, the above results show that the tight and high-valent cross-linking of membrane proteins leads to unusually fast internalization of protein.

In conclusion, the present inventors prepared a monomeric avidin-like protein that showed almost multimeric avidin-like binding stability against various biotin conjugates. Off-rates of MA are often slower than those of dimeric rhizavidin, and even comparable to those of tetrameric avidin proteins at room temperature. The MA of the present invention offers the first practically applicable monomeric avidin linker, which allows truly monomeric biotin labeling with minimal perturbation. In addition, the possibility of fabricating new high-valent avidin probes with designed orientations and valencies (such as 24-meric MAFt) will greatly diversify avidin/biotin linking strategies to build new bio-structures and nanostructures.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A monomeric avidin-like protein having a strong and stable biotin-binding ability, comprising the amino acid sequence of SEQ ID NO: 1, wherein the 67$^{th}$, 71$^{st}$, 82$^{nd}$, 84$^{th}$, 101$^{st}$, and 105$^{th}$ amino acid residues of SEQ ID NO: 1 are substituted with charged and hydrophilic amino acids, wherein the charged and hydrophilic amino acids are selected from the group consisting of aspartic acid, lysine, asparagine, glutamine, and arginine.

2. The monomeric avidin-like protein of claim 1, wherein the amino acid sequence of SEQ ID NO: 1 is derived from a monomer constituting rhizavidin, which is a dimeric avidin.

3. The monomeric avidin-like protein of claim 1, wherein the monomeric avidin-like protein comprises the amino acid sequence of SEQ ID NO: 2.

4. The monomeric avidin-like protein of claim 1, wherein the 23$^{rd}$, 46$^{th}$, and 115$^{th}$ amino acid residues of SEQ ID NO: 1 are further substituted with amino acids selected from the group consisting of histidine, glutamic acid, and tryptophan.

5. The monomeric avidin-like protein of claim 4, wherein the monomeric avidin-like protein comprises the amino acid sequence of SEQ ID NO: 3.

6. The monomeric avidin-like protein of claim 4, wherein the monomeric avidin-like protein has an off-rate of $0.5 \times 10^{-5}$ s$^{-1}$ to $7.0 \times 10^{-5}$ s$^{-1}$ with respect to the binding affinity to a biotin conjugate.

7. The monomeric avidin-like protein of claim 6, wherein the off-rate is measured at a temperature of 23-45° C.

8. The monomeric avidin-like protein of claim 6, wherein the biotin conjugate is a conjugate of biotin and a protein, a conjugate of biotin and a peptide, or a conjugate of biotin and a nucleic acid.

9. A protein conjugate comprising: a multimeric protein; and two or more of the monomeric avidin-like proteins of claim 1, the protein conjugate having a multivalent binding ability to biotin.

10. The protein conjugate of claim 9, wherein the multimeric protein is ferritin.

11. A nucleic acid molecule encoding the monomeric avidin-like protein of claim 1.

12. A method for producing a monomeric avidin-like protein with a biotin binding ability, the method comprising:
    (a) transforming a host cell with a recombinant vector comprising the nucleic acid molecule of claim 11; and
    (b) culturing the transformant to express a monomeric avidin-like protein with a biotin binding ability.

* * * * *